US006703346B2

(12) United States Patent
Herold et al.

(10) Patent No.: US 6,703,346 B2
(45) Date of Patent: Mar. 9, 2004

(54) HERBICIDE COMPOSITIONS COMPRISING IMIDAZOLINONE ACID, METHODS OF PREPARATION, AND METHODS OF USE

(75) Inventors: Anthony E. Herold, Greeley, CO (US); Scott K. Parrish, Spokane, WA (US); Richard A. Beardmore, Windsor, CO (US)

(73) Assignee: Platte Chemical Co., Greeley, CO (US)

( * ) Notice: Subject to any disclaimer, the term of this patent is extended or adjusted under 35 U.S.C. 154(b) by 0 days.

(21) Appl. No.: 10/103,519

(22) Filed: Mar. 21, 2002

(65) Prior Publication Data

US 2003/0144147 A1 Jul. 31, 2003

Related U.S. Application Data

(60) Provisional application No. 60/325,289, filed on Sep. 26, 2001, provisional application No. 60/325,342, filed on Sep. 26, 2001, provisional application No. 60/325,343, filed on Sep. 26, 2001, and provisional application No. 60/361,016, filed on Feb. 28, 2002.

(51) Int. Cl.[7] .................. A01N 25/02; A01N 25/30; A01N 43/50; A01N 57/02
(52) U.S. Cl. .................. 504/128; 504/139; 504/253; 504/277
(58) Field of Search ..................... 504/128, 139, 504/277, 253

(56) References Cited

U.S. PATENT DOCUMENTS

| | | | |
|---|---|---|---|
| 3,755,339 A | 8/1973 | McKendry | 260/295 R |
| 3,761,486 A | 9/1973 | McGregor | 260/294.9 |
| 3,937,826 A | 2/1976 | Harris | 424/219 |
| 4,188,487 A | 2/1980 | Los | 548/301 |
| 4,445,925 A | 5/1984 | Young | 71/28 |
| 4,816,060 A * | 3/1989 | Steller et al. | 71/92 |
| 4,971,630 A | 11/1990 | Skaptason | 71/117 |
| 4,994,101 A | 2/1991 | Young | 71/83 |
| 5,118,338 A | 6/1992 | Moller | 71/86 |
| 5,189,414 A | 2/1993 | Tawara | 340/825.5 |
| 5,221,319 A | 6/1993 | Van Haften et al. | 504/114 |
| 5,268,352 A | 12/1993 | Dexter | 504/206 |
| 5,270,286 A | 12/1993 | Ong | 504/130 |
| 5,280,008 A | 1/1994 | Cahoy et al. | 504/116 |
| 5,288,692 A | 2/1994 | Young | 504/127 |
| 5,317,042 A | 5/1994 | Narayanan | 514/722 |
| 5,328,889 A | 7/1994 | Van Haften et al. | 504/116 |
| 5,416,067 A | 5/1995 | Van Haften et al. | 504/323 |
| 5,538,938 A * | 7/1996 | Duckworth | 504/130 |
| 5,565,409 A | 10/1996 | Sato et al. | 504/127 |
| 5,668,085 A | 9/1997 | Forbes et al. | 504/206 |
| 5,696,024 A * | 12/1997 | Szamosi et al. | 504/144 |
| 5,707,928 A | 1/1998 | Baker | 504/139 |
| 5,994,271 A | 11/1999 | Ravetta et al. | 504/206 |
| 6,069,115 A | 5/2000 | Pallett et al. | 504/270 |
| 6,071,857 A | 6/2000 | Vogt et al. | 504/116 |
| 6,156,705 A | 12/2000 | Mueninghoff | 504/363 |
| 6,165,939 A | 12/2000 | Agbaje et al. | 504/105 |
| 6,180,563 B1 | 1/2001 | Ruegg et al. | 504/128 |
| 6,180,566 B1 | 1/2001 | Nielsen et al. | 504/206 |
| 6,187,715 B1 | 2/2001 | Narayanan et al. | 504/118 |
| 6,207,617 B1 | 3/2001 | Gillespie | 504/206 |
| 2002/0107149 A1 | 8/2002 | Volgas et al. | 504/317 |

FOREIGN PATENT DOCUMENTS

| | | |
|---|---|---|
| CA | 1225533 | 8/1987 |
| DE | 2 328 192 | 1/1974 |
| EP | 0 100 440 | 2/1984 |
| EP | 0 163 598 | 4/1985 |
| EP | 0 216 126 | 4/1987 |
| EP | 0 217 125 | 4/1987 |
| EP | 0 243 522 | 11/1987 |
| EP | 0334041 | 9/1989 |
| EP | 0 357 553 | 3/1990 |
| EP | 0 433 577 | 6/1991 |
| EP | 0 454 968 | 11/1991 |
| EP | 0 641 161 | 10/1996 |
| EP | 0 703 724 | 2/2002 |
| GB | 2 230 955 | 11/1990 |
| GB | 2267825 | 12/1993 |
| WO | WO 92/21686 | 12/1992 |
| WO | WO94/19941 | 9/1994 |
| WO | WO96/08150 | 3/1996 |
| WO | WO98/17109 | 4/1998 |
| WO | WO99/55155 | 11/1999 |
| WO | WO00/42847 | 7/2000 |
| WO | WO00/67571 | 11/2000 |
| WO | WO01/52650 | 7/2001 |
| WO | WO02/11536 | 2/2002 |

OTHER PUBLICATIONS

PCT/US02/08952 International Search Report.
PCT/US02/08953 International Search Report.
PCT/US02/08830 International Search Report.
PCT/US02/08787 International Search Report.
PCT/US02/08952 Annex to Form PCT/ISA/206, Communication Relating to the Results of the Partial International Search.
PCT/US02/08953 Annex to Form PCT/ISA/206, Communication Relating to the Results of the Partial International Search.
Milton J. Rosen, "Surfactants and Interfacial Phenomena," John Wiley & Sons, pp. 239–240 (1978).
Briggs et al., "Physico–chemical Factors Affecting Uptake by Roots and Translocation to Shoots of Weak Acids in Barley," *Pesticide Science,* vol. 19, pp. 101–112 (1987).
Wyrill, J.B. et al., "Glyphosate Toxicity to Common Milkweed and Hemp Dogbane as Influenced by Surfactants," Weed Science, vol. 25, No. 3 pp. 275–287 (May 1977).

(List continued on next page.)

Primary Examiner—S. Mark Clardy
(74) Attorney, Agent, or Firm—Kagan Binder, PLLC

(57) ABSTRACT

Described are herbicide compositions (including suspension concentrates, herbicide compositions prepared therefrom), and others that include imidazolinone acid, which can optionally and preferably also include an acidifying agent, and methods of making and using such compositions.

46 Claims, No Drawings

OTHER PUBLICATIONS

Tomlin, C., Ed., The Pesticide Manual, Tenth Edition, p. 1338, (1995).

Chemical Abstracts, Turner et al., "Complexing agents as herbicide additives," Weed Res., vol. 18, No. 4, pp. 199–207 (1978) CA 89:158688.

Chemical Abstracts, McMullan, "Effect of adjuvant and acidifying agent on imazamethabenz efficacy," Can. J. Plant Sci., vol. 72, No. 4, pp. 1389–1392 (1992) CA 118:207455.

Chemical Abstracts, Zsoldos et al., "Effects of ph changes on ion and 2,4–D uptake of wheat roots," Dep. Plant Physiol., pp. 77–80 (1978) CA 92:192532.

Chemical Abstracts, Shone et al., "Absorption and translocation of 2,4–dichlorophenoxyacetic acid (2,4–D) by barley roots," Annu. Rep.—Agric. Res. Counc., pp. 32–33 (1973) CA 85:57935.

Chemical Abstracts, Sherrick et al., "Effects of adjuvants and environment during plant development on glyphosate adsorption and translocation in field bindweed," Weed Sci., vol. 34, No. 6, pp. 811–816 (1986).

* cited by examiner

HERBICIDE COMPOSITIONS COMPRISING IMIDAZOLINONE ACID, METHODS OF PREPARATION, AND METHODS OF USE

This application claims the benefit of U.S. Provisional Application Serial No. 60/325,289, U.S. Provisional Application Serial No. 60/325,342, and U.S. Provisional Application Serial No. 60/325,343, all filed Sep. 26, 2001, and the benefit of U.S. Provisional Application Serial No. 60/361,016, entitled Herbicide Compositions Comprising Imidazolinone Acid, Methods of Preparation, and Methods of Use, filed Feb. 28, 2002.

FIELD OF THE INVENTION

The invention relates to herbicide compositions comprising imidazolinone acid, including but not limited to suspension concentrates, methods of preparing such herbicide compositions, and methods of using each.

BACKGROUND

Commercially available herbicide compositions include a very large variety of active herbicide compounds. Such herbicide compositions can be prepared from different types of precursor compositions, and can be commercially available and used in a variety of different types of compositions, including, for example, compositions referred to as wettable powders, water dispersible granules, granules, aqueous solutions, water soluble powders, emulsifiable concentrates, oil-based flowables, concentrated emulsions, suspoemulsions, emulsions, suspensions, suspension concentrates, mixtures, dispersions, and microemulsions, as well as others. Any of these different types of compositions may have different advantages or disadvantages relating to factors such as the mode of application and the type of active ingredient included in the herbicide composition.

Examples of useful suspension concentrates are described in U.S. Pat. Nos. 6,207,617 B1 (Gillespie), 5,707,928 (Baker), and 5,268,352 (Dexter). Other exemplary suspension concentrates are described in Assignee's copending United States Patent Application "Herbicide Compositions Comprising Suspension Concentrate with Glyphosate Acid, Methods of Preparation, and Methods of Use,", having serial No. 60/325,343, filed on Sep. 26, 2001.

Examples of just a few available active herbicide compounds include those of the general class known as phenoxy herbicides, e.g., 2,4-dichlorophenoxyacetic acid (known as 2,4-D), MCPA acid, MCPP acid; those of the general class known as pyridine herbicides, (e.g., triclopyr, fluoroxypyr); those of the general class of benzoic acid herbicides, (e.g., dicamba acid); those of the general class of aryloxy phenoxy propionic acid herbicides, (e.g., fluzafop acid and quizolofop acid); water-insoluble diphenyl ether type herbicides (e.g., oxyfluorfen or acifluorfen); glyphosate compounds (N-(phosphonomethyl)glycine), e.g., in the acid form, referred to as glyphosate acid, or in a salt form such as the IPA salt form; imidazolinone herbicide compounds (e.g., imazethapyr, imazaquin, imazapyr, imazamethabenz, imazapic, or imazamox); as well as others.

Active herbicide ingredients such as these and others can be prepared from and used in the form of solid and liquid compositions including, as mentioned above, different forms of emulsions, suspensions, suspension concentrates, mixtures, dispersions, microemulsions, etc., and derivatives thereof such as diluted solutions or solutions including other added ingredients such as additional herbicides, surfactants, and acidifying agents.

Imidazolinones are a known active herbicide ingredient and are commercially available, for example, under the trade designations "ARSENAL", "CHOPPER", "STALKER" (imazapyr); "SCEPTER"; "IMAGE" (imazaquin); "ASSERT" (imazamethabenz); "CADRE", "PLATEAU" (imazapic); "PURSUIT" (imazethapyr); "RAPTOR", "ODESSEY" (imazamox).

Specifically with regard to imidazolinone herbicide compounds, this compound is understood to be available in a variety of chemically different forms including imidazolinone acid and imidazolinone salts.

Surfactants may be combined with active herbicide compounds, as mentioned above, to facilitate suspending the compound and provide a suspension concentrate. U.S. Pat. No. 6,207,617 (Gillespie) generally describes suspension concentrate compositions that includes a specific amount of active herbicide compound and a specific polyoxyethylene alkylether or polyoxyethylene alkenylether surfactant.

Acidifying agents may be combined with herbicide compositions to improve performance. Such herbicide compositions are described, for example, in U.S. Pat. No. 4,994,101 (Young), and in United States Patent Applications "Herbicide Microemulsion-Forming-Concentrates, Microemulsions, and Methods", "Herbicide Composition Comprising Herbicide Compound in Acid Form and Acidifying Agent,", and "Herbicide Compositions Comprising Suspension Concentrate with Glyphosate Acid, Methods of Preparation, and Methods of Use," having Ser. Nos. 10/103,455, 10/102,799, and 10/103,493, filed on even date herewith.

Always desirable are new forms of useful and effective herbicide compositions. Particularly desirable can be compositions that have improved efficacy or that can be produced more conveniently or efficiently, or without using organic solvents.

SUMMARY OF THE INVENTION

The invention relates to herbicide compositions that include active herbicide compound comprising an imidazolinone in acid form. The use of imidazolinone in its acid form provides efficiency because the acid form does not need to be converted to the imidazolinone salt form during processing or prior to application, as is often done with imidazolinone herbicide compounds, because the salt forms are more soluble in water. Instead, herbicide compositions that contain imidazolinone acid in the imidazolinone acid form, such as preferred suspension concentrates, can be simple and economical to produce, and can be efficiently distributed, prepared, and applied without taking steps to convert the imidazolinone herbicide out of its acid form. Additionally the neutral, acid form of the compound has better uptake by a target plant, and can be less susceptible to deactivation by hard water.

In one embodiment, herbicide compositions of the invention may include a suspension concentrate that includes an active imidazolinone acid herbicide compound, or derivatives of those suspension concentrates. The suspension concentrates can be used in their suspension concentrate form to control plant growth, or can be used to prepare derivative herbicide compositions for application to control plant growth. For example, the suspension concentrate can be diluted or combined with an aqueous acidifying agent, e.g., in a tank mix procedure or otherwise, to form a herbicide application composition, and can optionally be further combined with other ingredients such as an additional, different active herbicide compound.

Generally, it is desirable to produce herbicide compositions, including precursor compositions, easily and efficiently. Suspension concentrates have been found to be easily and efficiently producible with the use of one or more ingredients such as surfactants, dispersants, thickeners, etc., one or more of which, optionally in combination with one or more of mixing, agitation, and milling, etc., can allow imidazolinone acid particles to be suspended and/or dispersed in water to form a suspension concentrate. Preferred surfactants may include nonionic surfactant, anionic surfactant, cationic surfactant, and mixtures thereof. Preferred nonionic surfactant may include short chain alcohol ethoxylate surfactant. Preferred anionic surfactant may include sodium butyl naphthalene sulfonate, sodium di-n-butyl naphthalene sulfonate, sodium diisopropyl naphthalene sulfonate, sodium dimethyl naphthalene sulfonate, ethoxylated tristyrylphenol phosphate potassium salt, and mixtures thereof. Preferred cationic surfactant may include ethoxylated tallow amine.

Preferred suspension concentrate herbicide compositions of the invention can have benefits when compared to other forms of herbicide formulations, such as the absence of dust; reduction of toxicity or flammability, etc.; they can be prepared to contain essentially no organic solvent; they can exhibit increased efficacy, for example due to lower particle size; they benefit from a low packing volume as compared to other forms of herbicides such as powders; and the suspension concentrates are relatively easy to handle.

The invention also contemplates the independent general concept of using imidazolinone acid-containing herbicide compositions generally, in combination with an acidifying agent, especially certain types of acidifying agents, and especially to produce certain ranges of pH in a herbicide composition. Such herbicide compositions may be prepared from or comprise different types of herbicide or herbicide precursor compositions that are capable of containing an imidazolinone acid, for example, compositions such as wettable powders, water dispersible granules, granules, aqueous solutions, water soluble powders, emulsifiable concentrates, oil-based flowables, concentrated emulsions, suspo-emulsions, emulsions, suspensions, suspension concentrates, mixtures, dispersions, and microemulsions, as well as others. This aspect of the invention can advantageously provide improved efficacy of imidazolinone acid herbicide compounds. In one embodiment of the invention, a herbicide composition can comprise an imidazolinone acid active herbicide compound combined with acidifying agent, preferably to produce a herbicide composition having a pH below the pKa of the imidazolinone acid. Preferred herbicide application compositions can have a pH below about 7, or otherwise below the pKa of imidazolinone acid compound.

In one aspect, the invention relates to a herbicide composition that includes a suspension concentrate that includes an imidazolinone acid, and an acidifying agent other than sulfuric acid, in an amount so the pH of the composition is below the pKa of the imidazolinone acid.

Another aspect of the invention relates to a herbicide composition that includes an imidazolinone acid and an acidifying agent other than sulfuric acid, in an amount so the pH of the composition is below the pKa of the imidazolinone acid. Preferred herbicide compositions can comprise or be prepared from suspension concentrates.

Another aspect of the invention relates to a suspension concentrate, preferably an aqueous suspension concentrate, that includes an imidazolinone acid and a short chain alcohol ethoxylate nonionic surfactant.

Another aspect of the invention relates to a suspension concentrate, preferably an aqueous suspension concentrate, that includes an imidazolinone acid and anionic surfactant.

Another aspect of the invention relates to a suspension concentrate that includes imidazolinone acid and surfactant, and from greater than 30 parts by weight imidazolinone acid to about 50 parts by weight imidazolinone acid, per 1 part by weight surfactant.

Another aspect of the invention relates to a herbicide composition comprising:
    aqueous suspension concentrate comprising
        about 25 to about 45 weight percent imidazolinone acid, and
        about 0.5 to about 1.5 weight percent surfactant selected from the group consisting of: short chain alcohol ethoxylate nonionic surfactant, anionic surfactant, cationic surfactant, and mixtures thereof, and
        about 40 to about 60 parts by weight water; and
    acidifying agent selected from the group consisting of sulfuric acid, hydrochloric acid, nitric acid, acetic acid, phosphoric acid, perchloric acid, and polyphosphoric acid, an adduct of sulfuric acid and urea, and combinations thereof, in an amount so the pH of the composition is below the pKa of the imidazolinone acid.

Another aspect of the invention relates to a herbicide composition comprising:
    aqueous suspension concentrate comprising
        about 25 to about 45 weight percent imidazolinone acid, and
        about 0.5 to about 1.5 weight percent surfactant selected from the group consisting of: nonionic surfactant, anionic surfactant, cationic surfactant, and mixtures thereof, and
        about 40 to about 60 parts by weight water; and
    acidifying agent selected from the group consisting of hydrochloric acid, nitric acid, acetic acid, phosphoric acid, perchloric acid, and polyphosphoric acid, an adduct of sulfuric acid and urea, and combinations thereof, in an amount so the pH of the composition is below the pKa of the imidazolinone acid.

Still another aspect of the invention relates to a method of killing or controlling unwanted vegetation growth, the method including the steps of 1) preparing a herbicide composition that includes imidazolinone acid and an amount of acidifying agent, other than sulfuric acid, to reduce the pH of the herbicide composition to a pH below the pKa of the imidazolinone acid, and 2) applying the herbicide composition to control plant growth.

Still a further aspect of the invention relates to a method of killing or controlling unwanted vegetation growth, the method including the steps of 1) preparing a herbicide composition that includes a suspension concentrate that includes an imidazolinone acid and a surfactant selected from the group consisting of a short chain alcohol ethoxylate nonionic surfactant, an anionic surfactant, a cationic surfactant, and mixtures thereof, and 2) applying the herbicide composition to control plant growth.

Yet another aspect of the present invention relates to a method of preparing an aqueous suspension concentrate that includes imidazolinone acid, the method including the steps of 1) combining imidazolinone acid particles with water, surfactant comprising: a short chain alcohol ethoxylate nonionic surfactant, anionic surfactant, cationic surfactant, and mixtures thereof, 2) mixing or agitating the water, imidazolinone acid particles, and surfactant, and 3) wet milling the water, imidazolinone particles and surfactant to produce a suspension concentrate.

Yet another aspect of the invention relates to a method of preparing herbicide composition that includes imidazolinone acid, the method including the steps of 1) combining imidazolinone acid particles with water and surfactant, 2) mixing or agitating the water, imidazolinone acid particles, and surfactant, 3) wet milling water the imidazolinone acid particles and surfactant, to produce a suspension concentrate, and 4) combining the aqueous suspension concentrate with acidifying agent in an amount to produce a herbicide composition having a pH below the pKa of the imidazolinone acid.

DETAILED DESCRIPTION

Imidazolinone Acids

Imidazolinone compounds, and chemical derivatives thereof, are a known type of active herbicide compound. Imidazolinone compounds are a class of highly potent, environmentally benign, crop selective herbicides. The imidazolinone class of herbicides are highly desirable for the selective control of a wide variety of grass and broadleaf weeds in the presence of agricultural crops, and in non-crop areas such as turf forestry. Imidazolinone is generally available in either the acid or salt form. The salt forms are considered to be generally soluble in water, whereas the acid forms are considered to be generally insoluble in water.

The present invention relates to herbicide compositions that include imidazolinone in the acid form.

The term "herbicide composition" refers to compositions that include a herbicide compound, specifically here, imidazolinone acid. Herbicide compositions of the invention can include different types of precursor compositions, for example, compositions referred to as wettable powders, water dispersible granules, granules, aqueous solutions, water soluble powders, emulsifiable concentrates, oil-based flowables, concentrated emulsions, suspo-emulsions, emulsions, suspensions, suspension concentrates, mixtures, dispersions, and microemulsions, as well as others. In one important embodiment, herbicide compositions of the invention may include a suspension concentrate that includes the active herbicide compound imidazolinone, in the acid form.

Imidazolinone in the acid form is considered to be generally an insoluble active herbicide compound. This means, for example, depending on temperature and pH, that imidazolinone acid can be soluble in water or acidic water only up to a few weight percent, meaning that approximately 100 grams of an aqueous solution can dissolve only approximately a couple of grams of imidazolinone acid, e.g., approximately 1 gram, or one weight percent.

Examples of imidazolinone acids include imazethapyr acid, imazaquin acid, imazapyr acid, imazamethabenz acid, imazapic acid, imazamox acid, and combinations thereof. Imazethapyr acid has the molecular formula $C_{15}H_{19}N_3O_4$ and is commercially available generally in the form of a powdered solid, under the trade designation "PURSUIT." Imazaquin acid has the molecular formula $C_{17}H_{17}N_3O_3$ and is commercially available generally in the form of a powdered solid, under the trade designation "SCEPTER" and "IMAGE." Imazapyr acid has the molecular formula $C_{13}H_{15}N_3O_3$ and is commercially available generally in the form of a powdered solid, under the trade designation "ARSENAL," "CHOPPER," and "STALKER." Imazamethabenz acid has the molecular formula $C_{15}H_{18}N_2O_3$ and is commercially available generally in the form of a powdered solid, under the trade designation "ASSERT." Imazapic acid has the molecular formula $C_{14}H_{17}N_3O_3$ and is commercially available generally in the form of a powdered solid, under the trade designation "CADRE" and "PLATEAU." Imazamox acid has the molecular formula $C_{15}H_{19}N_3O_4$ and is commercially available generally in the form of a powdered solid, under the trade designation "RAPTOR" and "ODESSEY."

The pKa of each of these is understood to refer to the negative logarithm (base 10) of the equilibrium constant K for the reaction of the herbicide compound between its acid form and its neutral form. Methods of determining pKa for a herbicide compound will be readily understood by the skilled artisan. Exemplary imidazolinone acids described herein can generally have a pKa below about 7, especially below about 5 or 4, for example, the pKa of imazamethbenz is approximately 2.9, the pKa of imazapyr is approximately 2 or 3, the pKa of imazaquin is approximately 3.8, and the pKa of imazethapyr is approximately 3.9.

The use of imidazolinone acids can be advantageous because the acid form does not need to be converted to the imidazolinone salt form during processing or prior to application, as is often done with imidazolinone herbicide compounds, because the salt forms are more soluble in water. Instead, herbicide compositions that contain imidazolinone acid in the imidazolinone acid form, such as preferred suspension concentrates, can be simple and economical to produce, and can be efficiently distributed, prepared, and applied without taking steps to convert the imidazolinone herbicide out of its acid form. In addition, the acid form of imidazolinone compounds, due to its uncharged state, can be advantageously less affected or unaffected by hard water, e.g., less susceptible to de-activation by hard water.

Suspension Concentrates

In one preferred embodiment of the invention, a herbicide composition includes a suspension concentrate comprising imidazolinone acid. The term "suspension concentrate" as used herein, means a composition also sometimes referred to as an "aqueous flowable" or a "water-based flowable" composition, which compositions are known in the herbicide art and include or consist of particles of a generally insoluble solid active herbicide compound in suspension (preferably concentrated suspension) in water. Exemplary suspension concentrates that contain a different active herbicide, glyphosate acid, are described in Assignee's copending United States Patent Application "Herbicide Compositions Comprising Suspension Concentrate with Glyphosate Acid, Methods of Preparation, and Methods of Use,", having Ser. No. 10/103,493, filed on even date herewith.

The suspension concentrates described herein can be produced with particles of imidazolinone acid compounds by suspending and preferably dispersing the particles in water with the assistance of other ingredients such as surfactant (also referred to as "wetting agents"), dispersant, and other optional ingredients.

The imidazolinone acid should be in the form of particles that exhibit physical characteristics such as size, shape, surface features, etc., that will allow the imidazolinone acid particles to be suspended in the form of a suspension concentrate, preferably an aqueous suspension concentrate. The particle size range can vary depending on factors such as the other ingredients used to prepare the suspension concentrate and their respective amounts, but exemplary particles may be in the size range below about 10 microns, for example in the range from about 4 to about 8 micrometers in diameter or from about 5 to about 7 micrometers in diameter.

Herbicide compositions of the invention include imidazolinone acid in a useful amount. Useful amounts of imidazolinone acid in any particular composition can depend on the intended application (including the plant to be controlled or the crop to be protected), the mode of application (e.g., field or aerial spraying or application from a hand-held spray applicator, or other technique), the method of any preparation of a herbicide application composition, the amounts and identities of other ingredients added to the herbicide composition, etc. For example, an amount that, in combination with one or more other ingredients described herein (e.g., such as surfactant and/or dispersant) will allow suspension and preferably dispersion of the imidazolinone acid particles to provide a suspension concentrate. In one embodiment, useful amounts of imidazolinone acid compound in a suspension concentrate may be, for example, in the range from about 20 to about 60 weight percent imidazolinone acid based on the total weight of the suspension concentrate. In another embodiment, useful amounts of imidazolinone acid compound in a suspension concentrate etc. According to the invention, the surfactant can be any surfactant or combination of surfactants (e.g., blends of anionic, nonionic or cationic surfactants), useful to produce the suspension concentrate.

According to the invention, dispersant can also be used to facilitate preparation of a suspension concentrate containing imidazolinone acid particles. A dispersant can stabilize and maintain a separation between suspended particles, which otherwise may have a tendency to flocculate due to attractive forces. Dispersants can provide repulsive forces to balance the tendency to flocculate. Useful dispersants include anionic and nonionic dispersants. An example of a useful, commercially available nonionic dispersant is Tersperse 4892 from Huntsman.

Examples of useful surfactants and dispersants are listed in the table below.

| TRADE NAME | COMMON NAME | FUNCTION | GENERAL CLASSIFICATION |
| --- | --- | --- | --- |
| Tomadol 1-5 | 11 carbon 5 mole linear alcohol | wetting agent | nonionic |
| Surfonic L12-6 | 12 carbon 6 mole linear alcohol | wetting agent | nonionic |
| Trymeen 6607 | 20 mole tallow amine | wetting agent/adjuvant | cationic |
| Stepfac 8170 | phosphate ester | dispersant/adjuvant | anionic |
| Surfonic PE 1218 | phosphate ester | dispersant/adjuvant | anionic |
| Surfonic OP-70 | 7 mole octylphenol | wetting agent/adjuvant | nonionic |
| Tergitol NP-9 | 9 mole nonylphenol | wetting agent/adjuvant | nonionic |
| Soprophor 796P | tristerol phenol EO/PO | dispersant | nonionic |
| Soprophor FLK | tristerolphenol potassium phosphate | dispersant | anionic |
| Polyfon H | sodium lignosulfonate | dispersant | anionic |
| Morwet D425 | napthalene formaldehyde condensant | dispersant | anionic |
| Morwet IP | naphthalene sulfonates | wetting agent | anionic |
| Pluronic L1061 | block copolymer | dispersant | nonionic |
| Tersperse 4984 | block copolymer/alcohol ethoxylate | dispersant, wetting | nonionic |
| Tersperse 2500 | surfactant | dispersant | anionic |
| Surfonic DOS60 | sulfosuccinate | wetting agent | anionic |
| LI-700 | lecithin derivative | adjuvant | nonionic |
| Goodrite K732 | polyacrylic acid | dispersant | anionic | may be, for example, in the range from about 25 to about 45 weight percent imidazolinone and based on the total weight of the suspension concentrate. Exemplary concentrations of suspension concentrates prepared according to the invention can include 3 pounds of imidazolinone acid per gallon, and 4 pounds of imidazolinone acid per gallon. Other concentrations of imidazolinone acid will also be useful.

Other ingredients may be used to prepare useful suspension concentrates and herbicide compositions. Exemplary other ingredients include surfactant, dispersant, thickener, and antifoaming agent.

As used in the present invention, surfactant can be used for several purposes. In one embodiment, surfactant is used to at least facilitate suspending the imidazolinone acid particles in a suspension concentrate by helping to wet and/or disperse the solid particles. Surfactants can lower the surface tension of the water, helping to replace air on the surface of particles of the imidazolinone acid with water, thereby suspending the particles. If milling is required (see below), during milling, new particle surfaces are created by mechanical breakdown of solid imidazolinone particles and surfactant adsorbs onto the particle surfaces to give rise to fluidity of the suspension.

A very large variety of surfactants are known and commercially available, including such different classes as anionic surfactants, nonionic surfactants, cationic surfactants, ionic surfactants, and amphoteric surfactants, An anionic surfactant is a surface-active molecule in which an active portion of a lipophilic portion of the molecule forms a negative ion (i.e., anion) when placed in aqueous solution. Exemplary anionic surfactants include phosphoric acid ester surfactants (sometimes referred to as "phosphate ester" surfactants), sodium alkyl naphthalene sulfonate surfactants, and ethoxylated tristyrylphenol phosphate salts.

Exemplary sodium alkyl naphthalene sulfonate surfactants include sodium butyl naphthalene sulfonate, sodium di-n-butyl naphthalene sulfonate, sodium diisopropyl naphthalene sulfonate, sodium dimethyl naphthalene sulfonate, and mixtures thereof Sodium butyl naphthalene sulfonate is commercially available, for example, under the trade name "MORWET B" from Witco/Crompton, Greenwich, Conn. Sodium di-n-butyl naphthalene sulfonate is commercially available, for example, under the trade name "MORWET DB" from Witco/Crompton, Greenwich, Conn. Sodium diisopropyl naphthalene sulfonate is commercially available, for example, under the trade name "MORWET IP" from Witco/Crompton, Greenwich, Conn. Sodium dimethyl naphthalene sulfonate surfactant is commercially available, for example, under the trade name "SELLOGEN HR" from Henkle Corp., Cincinnati, Ohio.

An exemplary ethoxylated tristyrylphenol phosphate potassium salt surfactant is commercially available, for example, under the trade name "SOPROPHOR FLK" from Rhodia, Cranbury, N.J.

A nonionic surfactant is a surface-active molecule that does not contain ionizable polar end groups but does contain hydrophilic and lipophilic portions. Exemplary nonionic surfactants include polyoxyethylene alkylether or alkenylether surfactants. Nonionic surfactant used to prepare a suspension concentrate as described herein may include long or short chain alcohol ethoxylate surfactant. The alcohol ethoxylate surfactant may be branched or linear.

An example of a useful nonionic polyoxyalkylene surfactant includes alcohol ethoxylate having the general formula:

$$R-O-((CH_2)_xO)_y-H$$

wherein R may be "long" or "short" chain and "branched" or "linear" alkyl. R preferably can be a "short chain" branched or linear alcohol, meaning that it can have from about 3 to 23 or fewer carbon atoms. With respect to the oxyalkylene, x can preferably be in the range from about 2 to 5, preferably from about 2 to 4 (e.g., 2 or 3, for a polyoxyethylene or polyoxypropylene, respectively) and y can preferably be in the in the range from 5 to 25.

Examples of useful short chain nonionic polyoxyalkylenes include linear alcohol polyoxyethylenes having the general formula:

$$CH_3(C_2H_4)_mO(C_2H_4O)_nH$$

wherein $CH_3(C_2H_4)_m$ is a short chain linear alkyl having from about 3 to 23 or fewer carbon atoms (i.e., m can be in the range from about 1 to 11 carbon atoms), and n is in the range from about 5 to 25.

Another example is short chain nonionic polyoxypropylenes having the general formula:

$$CH_3(C_2H_4)_mO(C_3H_6O)_nH,$$

wherein $CH_3(C_2H_4)_m$ is a short chain linear alkyl having from about 3 to 23 or fewer carbon atoms (i.e., m can be in the range from about 1 to 11 carbon atoms), and n can preferably be in the range from about 5 to 25.

Exemplary short chain linear alcohol ethoxylate surfactant are commercially available, for example, under the trade names "SURFONIC L12-6" from Huntsman, Austin, Tex., "SURFONIC L24-7" from Huntsman, Austin, Tex., "TERGITOL 15-S-7", "TERGITOL 24-L-60", "ALPHONIC 1012-60", "ALPOHONIC 1414-60", "BIOSOFT ET 630," from Stepan Company, Chicago, Ill., and "GENOPAL 24-L-60."

Other exemplary surfactants include polyethylene glycol, fatty acid ethoxylates, phosphate esters, octyl phenol ethoxylates, and nonyl phenol ethoxylates.

Useful polyethylene glycol surfactants are commercially available, for example, under the trade names "ADEKA PEG" from Asahi Denka Kogyo, Tokyo, Japan.

Useful fatty acid ethoxylate surfactants are commercially available, for example, under the trade names "NINEX MT-610", "NINEX MT-615", and "NINEX MT-630" from Stepan, Northfield, Ill.

Useful phosphate ester surfactants are commercially available, for example, under the trade names "STEPFAC 8180", "STEPFAC 8181", and "STEPFAC 8182" from Stepan.

Useful octyl phenol ethoxylate surfactants are commercially available, for example, under the trade name "MAKON OP-9" from Stepan, Northfield, Ill.

Useful nonyl phenol ethoxylate surfactants are commercially available, for example, under the trade names "MAKON 4", "MAKON 6", "MAKON 8", "MAKON 10", "MAKON 12", and "MAKON 14" from Stepan, Northfield, Ill.

A cationic surfactant is a surface-active molecule in which an active portion of a lipophilic portion of the molecule forms a positive ion (i.e., cation) when placed in aqueous solution. In one embodiment, exemplary cationic surfactant includes ethoxylated tallow amine.

Suspension concentrates of the invention include surfactant in a useful amount. Useful amounts of surfactant ("surfactant" refers to one or a combination of surfactants) can be any useful amount, such as an amount that, in combination with one or more other ingredients described herein (e.g., such as dispersant) will allow preparation of a useful herbicide composition. Useful amounts of surfactant will be apparent to the skilled artisan based on this overall description. For example, useful amounts of surfactant can depend on the intended application (including the plant to be controlled or the crop to be protected), the mode of application (e.g., field or aerial spraying or application from a hand-held spray applicator, or other technique), the method of any preparation of a herbicide application composition, the amounts and identities of other ingredients added to the herbicide composition, etc. For example, an amount that, in combination with one or more other ingredients described herein (e.g., imidazolinone acid, dispersant, thickener) will allow suspension and preferably dispersion of the imidazolinone acid particles to provide a suspension concentrate. Useful amounts of surfactant in a suspension concentrate may be in the range from about 0.5 to about 1.5 weight percent surfactant based on the total weight of the suspension concentrate. Stated differently, useful amounts of imidazolinone acid and surfactant in a suspension concentrate may be, for example, from greater than 30 parts by weight imidazolinone acid to about 50 parts by weight imidazolinone acid, per 1 part by weight surfactant, e.g., from 31 to 45 parts by weight imidazolinone acid per 1 part by weight surfactant. In a particular embodiment, useful amounts of imidazolinone acid and short chain alcohol ethoxylate nonionic surfactant in a suspension concentrate may be, for example, from greater than 30 to about 50 parts by weight imidazolinone, per 1 part by weight short chain alcohol ethoxylate nonionic surfactant.

The amount of dispersant used in a suspension concentrate can be any useful amount that will allow the preparation of a herbicide composition. In one embodiment, a useful amount of dispersant can be an amount that will allow the preparation of a suspension concentrate, and that may help to stabilize a suspension concentrate, e.g., by preventing flocculation. Useful amounts may depend on the type of dispersant and the composition of the herbicide composition, and will be apparent to the skilled artisan. In one embodiment, useful amounts of dispersant in a suspension concentrate may be, for example, in the range from about 2 to about 5 weight percent dispersant based on the total weight of the suspension concentrate.

Dispersant may be combined with other ingredients (e.g., anionic, nonionic, or cationic surfactants) to allow preparation of a useful suspension concentrate, such as by aiding the stabilization of a suspension concentrate, e.g., by preventing flocculation. Useful combinations of dispersant and other ingredients may depend on the type of dispersant and other ingredient (e.g., anionic dispersant, nonionic dispersant, anionic surfactant, nonionic surfactant), and the composition of the, for example, suspension concentrate, and will be apparent to the skilled artisan. In one embodiment, a useful combination of dispersant and other ingredients in a suspension concentrate include anionic dispersant and anionic surfactant. In another embodiment, a useful combination of dispersant and other ingredients in a suspension concentrate include anionic dispersant and nonionic surfactant. In another embodiment, a useful combination of dispersant and other ingredients in a suspension concentrate include nonionic dispersant and anionic surfactant. In still another embodiment, a useful combination of dispersant and other ingredients in a suspension concentrate include nonionic dispersant and nonionic surfactant.

Other ingredients, additives, active herbicide compounds, or adjuvants can also be included in a suspension concentrate according to the invention, as will be appreciated by those skilled in the relevant arts. For example, an antifreeze may be useful, such as propylene glycol or other low molecular weight alcohols or polyols, in an amount to reduce the freezing point of a suspension concentrate. The amount of the antifreeze can be any amount that is useful, as will be understood by the skilled artisan. Exemplary amounts of antifreeze in a herbicide composition (e.g., suspension concentrate) can be below about 20 weight percent based on the total weight of the suspension concentrate, for example from 1 to about 15 weight percent, or from about 5 to about 10 weight percent.

Thickeners can be included in the suspension concentrate to provide gravitational stabilization by increasing viscosity. Useful thickeners include chemical compounds and polymeric materials that will be known to and understood by the skilled artisan, and include, generally, natural and synthetic starches, gums, and other types of chemical compounds that will increase the viscosity of a solution. Thickening agents are well known in the chemical and polymer arts, and include, inter alia, polyacrylamides, cellulosic resins and functionalized cellulosic resins, polyacrylic acids, polyethylene oxides, and the like. Commercially available examples include Kelzan and Rhodaopl 23 xanthan gums, Attagel 50 and Attaflow FL clays, Carbopol 910 polyacrylic acid polymer, Kelcosol sodium alginate, and Bentolite purified Bentonite.

A useful amount of thickener will result in increased viscosity and stability, without causing viscosity build that would be excessive for application of the composition as a herbicide. Exemplary amounts of thicker in a herbicide composition (e.g., suspension concentrate) can be below about 5 or 10 weight percent, based on the total weight of the suspension concentrate, may generally be useful. Preferred amounts may be less 0.5 weight percent for gums or cellulose resins.

Another additional ingredient that can be used in the suspension concentrate may include an antifoaming agent. Antifoaming agents are well understood in the chemical and herbicide arts, and a variety of useful examples are commercially available. Antifoam agents are substances such as silicones, organic phosphates, and alcohols that inhibit the formation of bubbles in a liquid by reducing surface tension. One specific example of a commercially available antifoam agent is SAG 10 (a 10% silicone in water), from Witco OSI. The amount of antifoaming agent used in a suspension concentrate will also be apparent to the skilled artisan, with typical amounts being less than 1 percent by weight, e.g., less than 0.5 percent by weight.

Additional active herbicide compounds can also be included in the suspension concentrate. Preferably, additional active herbicide compounds can be compounds present in an acid form, such as any one or more acid form herbicides described, e.g., in Applicants' copending U.S. patent applications "Herbicide Microemulsion-Forming-Concentrates, Microemulsions, and Methods" "Herbicide Composition Comprising Herbicide Compound in Acid Form and Acidifying Agent,"; and "Herbicide Compositions Comprising Suspension Concentrate with Glyphosate Acid, Methods of Preparation, and Methods of Use,", having Ser. Nos. 10/103,455, 10/102,799, and 10/103,493, filed on even date herewith, specifically including glyphosate acid active herbicide as well as all other acid herbicide compounds listed therein, or still other herbicides capable of existing in an acid form.

Other useful additives or adjuvants that can be used in a suspension concentrate according to the present invention may include other surfactants, antimicrobial agents, anticorrosion agents, acids or acidifying agents, and other ingredients. Surfactants having functions of wetting, spreading, or penetrating, preferably to improve efficacy of a herbicide composition, may also be added or can be added when a tank mix is made for application. Organic solvents may be included in a herbicide composition (e.g., suspension concentrate) if desired, but are generally not used or needed.

Suspension concentrates of the invention may include water in any useful amount. For example, a useful amount of water can be an amount that in combination with one or more other ingredients described herein (e.g., such as surfactant and/or dispersant) will provide a suspension concentrate by allowing suspension and preferably dispersion of the imidazolinone acid particles. Relative amounts of water and the other ingredients used to prepare a suspension concentrate can be any amounts that produce a useful herbicide composition in the form of a suspension concentrate. Relative amounts of different ingredients (imidazolinone acid, surfactant, etc.) in any particular composition can depend on the intended application (including the plant to be controlled or the crop to be protected), the mode of application (e.g., field or aerial spraying or application from a hand-held spray applicator, or other technique), the method of any preparation from a suspension concentrate to a herbicide application composition, the amounts and identities of other ingredients added to a herbicide composition (e.g., suspension concentrate), etc. In one embodiment, a useful amount of water within a suspension concentrate can be from about 40 to about 60 parts by weight water, preferably from about 40 to 55 parts by weight water. The amount of water for any suspension concentrate will relate to the concentration; a 3 pound per gallon suspension concentrate may have a lower amount of water per pound than a 4 pound per gallon suspension concentrate.

Suspension concentrate according to the invention may or may not include organic solvent. Preferred suspension concentrates are aqueous, meaning they contain essentially no organic solvent. "Essentially no organic solvent" as used in the present invention means a small amount of organic solvent relative to the amount of other ingredients, for example, less than 5 percent by weight, preferably less than 2 percent by weight, more preferably less than 1 percent by weight, and even more preferably less than 0.5 percent by weight.

Still other ingredients can also be added to a suspension concentrate of the invention to produce a derivative herbicide composition or herbicide application composition. These added ingredients may be useful in the herbicide composition for purposes of dilution, stability, pH adjustment, anti-foaming, or to otherwise facilitate application or increase efficacy. These other ingredients may be added to the suspension concentrate or derivative herbicide composition at any time and in any order, as desired or convenient. Exemplary additional ingredients include water, antifoaming agents, acidifying agents, anticorrosion agents, etc.

Herbicide Compositions Comprising Acidifying Agent

According to a broad concept of the invention, a herbicide composition comprising an imidazolinone acid can be used in combination with an acidifying agent. The herbicide composition can comprise or be prepare from any of a variety of forms of herbicide compositions, as will be found to be useful, such as but not limited to a suspension concentrate. Such herbicide compositions may be able to be prepared from or comprise any form of herbicide composition capable of containing an imidazolinone in its acid form, such as from among compositions referred to as wettable powders, water dispersible granules, granules, aqueous solutions, water soluble powders, emulsifiable concentrates, oil-based flowables, concentrated emulsions, suspoemulsions, emulsions, suspensions, suspension concentrates, mixtures, dispersions, and microemulsions, or others, as may be useful. Thus, the invention contemplates generally the use of herbicide compositions containing imidazolinone acid as an active herbicide compound, in combination with acidifying agent, to improve efficacy.

While wishing not to be bound by theory, it is believed that the direct application of the acid form of an imidazolinone, especially as part of a herbicide composition having a pH below the pKa of the imidazolinone acid compound, can effect improvements in plant control by one or both of the following mechanisms. First, a neutral (acid) molecule can have an easier time penetrating a cuticle on a plant, compared to a charged (salt) molecule. Secondly, an acidifying agent and a low pH of a herbicide composition can have a damaging effect on a plant's surface, thereby letting more herbicide penetrate the surface. Also, the neutral acid molecule can be less susceptible to de-activation by hard water.

Particularly preferred herbicide compositions can be formulated to include an acidifying agent in an amount sufficient to reduce the pH of the herbicide composition to below the pH of the imidazolinone acid, e.g., to a pH below about 7, preferably below about 5 or about 4. Preferably, the pH of the herbicide composition is below the pKa of the relevant imidazolinone acid. E.g., depending on the particular imidazolinone and its pKa, a pH of below about 4, 3.9, 3.8, 3.0, 2.9, or 2.0, may be preferred.

A variety of different acidifying agents can be useful in combination with different forms of imidazolinone-containing herbicide composition. The particular acidifying agent chosen and the amount used can be based on factors including the intended use or application of the herbicide composition (including the identity of the target undesirable plant growth and any nearby desirable plant growth) the method of application, physical and chemical properties of the herbicide application composition, and others. The acidifying agent may be any of a variety of suitable organic or inorganic acids, of any useful strength or concentration, that can be added to a herbicide composition, preferably without causing substantial or undue negative effects such as reaction with an ingredient of the herbicide composition such as the imidazolinone acid, precipitation, etc. It will be understood that an acidifying agent can be in a concentrated or diluted form, as necessary or desirable.

Examples of a certain type of acidifying agent are described in U.S. Pat. Nos. 4,445,925, 4,994,101, 5,288,692, (Young) the disclosures of which are incorporated herein by reference. Other exemplary acidifying agents are known, and still others are described in Assignee's copending United States Patent Application entitled "Herbicide Composition Comprising Herbicide Compound in Acid Form and Acidifying Agent," having Ser. No. 10/102,799, filed on even date herewith, and incorporated herein by reference. See also Assignee's copending United States Patent Applications entitled "Herbicide Compositions Comprising Suspension Concentrate with Glyphosate Acid, Methods of Preparation, and Methods of Use,", and "Herbicide Microemulsion-Forming-Concentrates, Microemulsions, and Methods," having Ser. Nos. 10/103,493 and 10/103,455, filed on even date herewith, and each of which is incorporated herein by reference.

One specific example of a useful type of acidifying agent includes adducts of sulfuric acid, and an "amide" according to the formula:

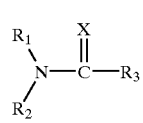

(1)

wherein X is chalcogen, and each of $R_1$, $R_2$ and $R_3$ is independently selected from hydrogen and organic radicals. As used herein, "amide" encompasses all compounds of formula (1) regardless of the chalcogen. The molar ratio of amide to acid is usually in the range of about ¼ to less than 2 so that at least some of the acid is present as the monoamide-acid adduct.

When $R_1$, $R_2$, and $R_3$ are organic radicals, they may be cyclic or acyclic, straight or branched chained, and can contain one or more heteroatoms such as sulfur, nitrogen, oxygen, phosphorus and the like. Further, $R_1$, $R_2$ and $R_3$ can contain one or more substituents such as thiol, hydroxy, nitro, amino, nitrile, amide, ester and halogen groups and others. Such organic radicals may contain aryl groups such as aralkyl and alkaryl groups. Certain preferred organic radicals can be free of olefinic or alkynyl unsaturation and can generally have up to about 20, preferably up to about 10 carbon atoms. Particularly preferred amides include urea, thiourea, formamide, dimethylformamide, biuret, triuret, thioform amide, and combinations of these.

The chalcogens are elements of Periodic Group VI-B and include oxygen, sulfur, selenium, tellurium, and polonium. Oxygen and sulfur can be preferred due to low cost, availability, low toxicity, and chemical activity, and oxygen is the most preferred.

A specific example of an adduct according to formula (1) can be the sulfuric acid/urea adduct:

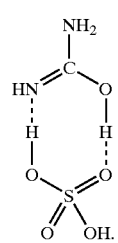

(2)

While the sulfuric acid/urea adduct of Formula 2 is specifically identified to be useful according to the invention, neither of that adduct nor sulfuric acid is specifically required to be the acidifying agent, and either of the adduct or sulfuric acid can be optionally included or entirely excluded from the methods and compositions of the invention.

Other examples of acidifying agents include acids such as sulfuric acid, phosphoric acid, hydrochloric acid, nitric acid, acetic acid (e.g., "glacial" acidic acid), perchloric acid, polyphosphoric acid, and any other acidifying agent that can be used to affect the pH of a herbicide composition, especially to prepare a herbicide composition including imidazolinone acid and having a pH below the pKa of an imidazolinone compound. These and other acidifying agents can be used alone or in combination. Various such acids are commercially available in different forms and concentrations, such as solids, liquid (aqueous) solutions, concentrated liquid solutions, etc., or can be prepared by one of skill in the chemical arts. Any such form of acidifying acid may be useful to reduce the pH of a herbicide composition comprising an imidazolinone acid, preferably without causing any undue negative effects. The chosen form of acidifying agent may be based on commercial availability, safety considerations, convenience, and the overall desired properties of the herbicide composition, its different ingredients (e.g., the herbicide compound), and its desired method of preparation and use.

The amount of acidifying agent added to a herbicide composition can be based on factors including the particular composition and chemistry of the herbicide composition, including the amounts and chemistries of ingredients such as the amount of water and the amounts and types of surfactant and herbicide compound; the form of the herbicide composition (e.g., suspension concentrate) and its concentration; the type of acidifying agent and its chemistry and strength (concentration); the desired pH; etc. Preferred amounts of any particular acidifying agent can be capable of improving the efficacy of the herbicide composition as applied, and particularly preferred amounts will be sufficient to produce an application composition having a pH below about 7.0, preferably below about 5 or about 4 (e.g., about 3.9, 3.8, 3.0, 2.9, 2.0), or otherwise below the pKa of imidazolinone acid compound.

Useful amounts of acidifying agent used in a herbicide composition will be quite varied considering the above factors. Relatively strong concentrations of liquid (aqueous) acidifying agent solutions such as 93% liquid sulfuric acid, 72% phosphoric acid, 85% polyphosphoric acid, 90% nitric acid, 99% glacial acetic acid, etc., can be added directly or can be first diluted and then added to a herbicide composition in an amount to bring the pH below about 7.0, preferably below about 5 or about 4 (e.g., about 3.9, 3.8, 3.0, 2.9, 2.0), or otherwise below the pKa of imidazolinone acid compound. In terms of volume percent, very generally speaking, useful amounts of aqueous acidifying agent such as those listed above can be below about 5 or 10 volume percent, e.g., for a suspension concentrate herbicide composition, in the range from about 0.01 to about 4 parts by volume aqueous acidifying agent based on the total by volume of a suspension concentrate and acidifying agent. Volumes of acidifying agent outside of this range may also be useful, depending on the form and concentration of the herbicide composition and the composition and strength of the acidifying agent, and useful amounts can be identified to achieve a desired pH of a herbicide composition.

Optionally, the herbicide composition comprising imidazolinone acid and acidifying agent can also include additional ingredients, including additional active herbicide compound, preferably additional active herbicide compound that can and does exist as an acid in the herbicide composition. The additional herbicide compound can be any of the acid form active herbicide compounds described in Applicants' copending U.S. patent applications "Herbicide Microemulsion-Forming-Concentrates, Microemulsions, and Methods" "Herbicide Composition Comprising Herbicide Compound in Acid Form and Acidifying Agent," and "Herbicide Compositions Comprising Suspension Concentrate with Glyphosate Acid, Methods of Preparation, and Methods of Use,", having Ser. Nos. 10/103,455, 10/102,799 and 10/103,493, filed on even date herewith. These specifically include glyphosate acid, glyphose acid in a suspension concentrate, microemulsions containing an acid form of active herbicide compound, any other forms of acid active herbicide compound, or any derivatives or combinations of these.

Methods of Making Herbicide Compositions

Certain methods of preparing herbicide compositions that contain imidazolinone acids will be recognized and understood by those of skill in the herbicide arts.

One method of preparing a herbicide composition containing an imidazolinone acid is to prepare a suspension concentrate (as discussed above) comprising imidazolinone acid.

One exemplary method of producing such a suspension concentrate herbicide composition starts with imidazolinone acid particles in the form of a wet cake or dry (granular, powder) acid, generally having a relatively large particle size (e.g., greater than about 10 microns). The wet cake or dry particles of that size can be mixed or dispersed into a liquid. This can be done, for example, by combining the imidazolinone acid particles with water and other ingredients with agitation or mixing to disperse the particles. For example, the imidazolinone acid particles can be added to water and one or more of surfactant, antifreeze, and antifoam, and mixed for about 20–30 minutes using a high-speed mixer to disperse the imidazolinone acid particles. Next, dispersant may be added to the mixture and mixed for about 10 minutes. The mixture of imidazolinone acid, water, and other ingredients can be further processed toward a suspension concentrate by methods that will process the imidazolinone acid particles into a form that allows suspension of the particles in the form of a suspension concentrate, for instance by reducing the size of the particles. Thus, a processing step can be to reduce the size of imidazolinone acid particles to a size that will allow the particles, in combination with one or more of the other ingredients described herein such as surfactant and/or dispersant, to be maintained in a stable suspension concentrate composition. An exemplary method of reducing the size of the imidazolinone acid particles is by using milling techniques, e.g., what is referred to as "wet milling." A typical such average particle size useful for providing a suspension concentrate can be below about 10 micrometers in diameter, for example in the range from about 4 to about 8 micrometers in diameter or from about 5 to about 7 micrometers in diameter. Any method of reducing particle size may be useful, such as by using an attrition mill, ball mill, sand mill, or other milling process. Further in such embodiment, a useful mechanical agitation step may be performed to add additional ingredients, if desired, such as thickening agent and antimicrobial agents.

After reduction of the particle size, the solution containing the suspended imidazolinone acid particles can be further combined with a thickener, by mixing the thickener into the solution.

The suspension concentrate can preferably be stable in the form of a suspension concentrate for a useful period, meaning that the suspension concentrate does not settle or otherwise transform out of the suspension concentrate form, and maintains the form of a suspension concentrate, for a useful amount of time. Useful periods of stability can depend on timing, e.g., between preparation, further processing of, and use (application) of the suspension concentrate, which time periods may vary greatly based on convenience, preference, inherent stability of the suspension, or other factors. If a suspension concentrate or a derivative form of the suspension concentrate can be applied in a short or very short period of time after preparation, longer-term stability is not required. Exemplary suspension concentrates of the invention can be stable at approximately room temperature and in substantially undisturbed and un-agitated environments for periods in excess of 6 or 12 months. Longer or shorter periods would also be useful.

Thus, an exemplary method of preparing a herbicide composition (suspension concentrate) including imidazolinone acid includes 1) combining imidazolinone acid particles with water and surfactant selected from the group consisting of: nonionic surfactant, anionic surfactant, cationic surfactant, and mixtures thereof, 2) mixing or agitating the water, imidazolinone acid particles, and surfactant, and 3) wet milling the water, imidazolinone acid particles, and surfactant to produce a suspension concentrate. Preferably, the suspension concentrate can be an aqueous suspension concentrate.

An exemplary general method of preparing a herbicide composition including a suspension concentrate comprising imidazolinone acid and further comprising an acidifying agent, includes: 1) combining imidazolinone acid particles with water and surfactant, 2) mixing or agitating the water, imidazolinone acid particles, and surfactant, 3) wet milling water, imidazolinone acid particles, and surfactant to produce a suspension concentrate, and 4) combining the suspension concentrate with acidifying agent other than sulfuric acid in an amount to produce a herbicide composition having a pH below the pKa of the imidazolinone acid. Preferred suspension concentrates can be aqueous suspension concentrates.

Other types or forms of herbicide compositions that comprise an imidazolinone acid will be able to be produced by methods known in the herbicide and herbicide composition arts, with the exact method depending in large part on the type of herbicide composition, e.g., whether the form is includes any one of a wettable powder, water dispersible granule, granule, aqueous solution, water soluble powder, emulsifiable concentrate, oil-based flowable, concentrated emulsion, suspo-emulsion, emulsion, suspension, mixture, dispersion, microemulsion, or another. Ingredients of such herbicide compositions can be combined by known methods, including one or a combination of mixing, agitating, dispersing, milling of the imidazolinone acid particles, and may be combined with other materials such as water, solvent, acidifying agent or other herbicide compound (especially active herbicide compounds in acid form), surfactants, dispersants, thickeners, other additives, etc. Any of the steps can be done in any order, such as milling the imidazolinone acid particles and adding the milled particles to other ingredients, such as water, surfactant, dispersant, thickener, solvent, etc., or by adding the particles to other ingredients, followed by wet milling. The herbicide composition comprising imidazolinone acid can be combined with other active herbicide compounds, preferably active herbicide compounds in acid form, in any manner.

Methods of Using

A herbicide composition as described, comprising imidazolinone in acid form, optionally in combination with an acidifying agent, including but not limited to a herbicide composition comprising or derived from a suspension concentrate, can be applied directly to a field or plant to control undesired plant growth, or can be combined with other ingredients to form a derivative herbicide composition for application. A herbicide composition having a concentration of herbicide compound (here, an imidazolinone acid) that would normally be applied to a field or plant to control undesired plant growth, can be referred to herein as a "herbicide application composition." "Herbicide application composition" refers to such a herbicide composition, as opposed, for example, to a herbicide composition having a higher concentration of herbicide compound, which could occur in preparation, storage, shipping, or sale of a herbicide composition.

Suspension concentrate compositions as described herein are capable of controlling plant growth if applied directly to a plant. Similarly, other concentrated forms of herbicide compositions described herein, e.g., comprising imidazolinone acid and an acidifying agent, optionally in combination with other active herbicide compounds, especially active acid herbicide compounds, can be useful when directly applied in concentrated forms. Yet it can be typical for reasons of efficiency, cost, convenience, techniques presently used in applying herbicide compositions, and environmental considerations, to use a relatively diluted form of herbicide composition to conveniently apply a specific and known amount of herbicide compound per acre or per other unit of application. By way of example, herbicide application compositions can include any herbicide composition having such a specific concentration of imidazolinone acid for application, e.g., to a field, and specifically include derivatives of suspension concentrates or derivatives of different forms of concentrated herbicide compositions, prepared by combining a suspension concentrate or other concentrated herbicide composition with one or more of water, acidifying agent, another herbicide, or other ingredients.

Herbicide compositions containing imidazolinone in acid form can be used for immediate and long-term, post-emergent control of a large variety of different forms of vegetation, in agricultural or non-agricultural settings. As an example, a suspension concentrate or other concentrated herbicide composition that contains an imidazolinone acid could be applied directly to plants for controlling plant growth, although this may include an unnecessarily potent concentration of the imidazolinone acid. Furthermore, it may as a general matter be difficult to uniformly apply a small amount of concentrated herbicide composition to a large area without dilution. A concentrated form would instead more likely be a product sold commercially as a herbicide concentrate product, which would be a composition that includes a relatively high concentration of imidazolinone acid active herbicide compound, as manufactured or packaged for sale, and which may typically be diluted or combined with other ingredients prior to use to form a herbicide application composition.

A concentrated herbicide composition comprising imidazolinone acid, e.g., a suspension concentrate, could be purchased by distributors or suppliers, or directly by consumers such as farmers, any of whom could add optional ingredients such as water, an acidifying agent (e.g., in the form of a solid, powder, or an aqueous solution, etc.), or another type of herbicide formulation or herbicide compound. The additional ingredients could, for example, be added and mixed in a tank immediately prior to application. A concentrated herbicide composition such as a suspension concentrate would typically be diluted with water. A typical dilution would be 1 pint of suspension concentrate in 15 gallons of water for ground application. Another typical dilution would be 1 pint of suspension concentrate in 3–5 gallons of water for application by air.

In one embodiment of a distribution system, a concentrated herbicide composition comprising an imidazolinone acid, e.g., a suspension concentrate, could be sold to farming product or nursery dealers, or the like, who could dilute the herbicide composition with water and/or add other ingredients such as an acidifying agent or other active herbicide. This could be particularly convenient if such a dealer normally kept a stock of acidifying agent such as phosphoric acid or sulfuric acid, etc. The herbicide composition combined with acidifying agent by the dealer could be sold to an end consumer who could use the composition as purchased or who could optionally further dilute the purchased composition or add other ingredients to the purchased composition such as an additional acid form herbicide compound by tank mixing.

A herbicide application composition can contain a useful amount of imidazolinone acid active herbicide compound, based on factors of efficacy, safety, application rate, etc. Similarly, a useful amount of herbicide application composition (containing the useful amount of imidazolinone acid) to be applied to a plant or a field, will be readily understood by those of skill, based, e.g., on desired efficacy, safety, application rate, and environmental factors, etc. The particular amount of imidazolinone acid in any specific herbicide application composition will depend on factors known and as described above. Advantageously, certain preferred herbicide application compositions of the invention, especially those that include an acidifying agent, and in particular those that also have a reduced pH (below about 7.0, preferably below about 5 or about 4 (e.g., about 3.9, 3.8, 3.0, 2.9, 2.0), or otherwise below the pKa of imidazolinone acid compound), can be applied at lower dosages or "application rates" (lower amounts of herbicide compound per plant or per acre) relative to other herbicide compositions containing other forms of imidazolinone (e.g., the salt form), or not at a reduced pH as described.

Examples of dosages ("application rates") of imidazolinone acid, especially as included in a herbicide compositions of a described relatively low pH, to a field, can be in the range from about 1/100 to about 6 pounds imidazolinone acid per acre, with dosages in the range from about 0.03 to 0.5 pounds per acre being particularly preferred. More resistant plants or different field environments may require higher concentrations and/or higher dosage rates, and a dosage rate may also be affected by factors such as the use of other active herbicide compounds. The preparation of herbicide application compositions suitable to apply useful dosages, based on the concentration of herbicide compound in a suspension concentrate or other concentrate comprising imidazolinone acid, will be understood by one of ordinary skill.

Inventive herbicide compositions can be applied using conventional aerial or ground spray techniques in field applications. The herbicide compositions can also be applied by any other useful technique, such as by spot-application to undesired plant growth using a hand-held applicator, or the like.

Vegetation that can be controlled using herbicide compositions of the invention generally include any type of vegetation that is or is known to be controlled by imidazolinone or imidazolinone acid herbicide compounds. The ingredients of the herbicide compositions, e.g., surfactant, dispersant, acidifying agent, water, additional active herbicide, etc., can be selected in view of the type of control desired (i.e. pre-emergent or post-emergent) and the type of vegetation to be controlled according to the known attributes of imidazolinone compounds, including imidazolinone acid.

In one embodiment, a method of killing or controlling unwanted vegetation growth includes 1) preparing a herbicide composition that includes imidazolinone acid and an amount of acidifying agent other than sulfuric acid to reduce the pH of the herbicide composition to a pH below the pKa of the imidazolinone acid and 2) applying the herbicide composition to control plant growth.

In another embodiment, a method of killing or controlling unwanted vegetation growth includes 1) preparing a herbicide composition that includes suspension concentrate which includes imidazolinone acid and surfactant selected from the group consisting of a short chain alcohol ethoxylate nonionic surfactant, anionic surfactant, cationic surfactant, and mixtures thereof, and 2) applying the herbicide composition to control plant growth. Optionally, such an embodiment may include acidifying agent to reduce the pH of the herbicide composition to below the pKa of the imidazolinone acid, the acidifying agent selected from the group consisting of sulfuric acid, hydrochloric acid, nitric acid, acetic acid, phosphoric acid, perchloric acid, and polyphosphoric acid, and a sulfuric acid adduct of the formula:

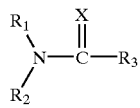

wherein X is chalcogen, and each of $R_1$, $R_2$, and $R_3$ is independently selected from hydrogen and organic radicals. In one particular embodiment acidifying agent is selected from the group consisting of phosphoric acid and an adduct of urea and sulfuric acid.

EXAMPLES

Examples 1–3

Examples of suspension concentrates according to the invention can contain 4 lb. imidazolinone acid per gallon and can be prepared from ingredients including those described in Examples 1–3. In examples 1–3 "AI" means "active ingredient."

Example 1

Example 1 is an exemplary suspension concentrate that includes a 4 lb. per gallon imidazolinone acid (imazethapyr acid), anionic surfactant, anionic dispersant, thickener, and anti-microbial agent.

TABLE 1

| Example 1 Ingredients | | | |
|---|---|---|---|
| Ingredient | % AI-Tech | % Weight | % AI |
| Water | | 44.90 | |
| SAG 30 Antifoam, Witco | | 0.3 | |
| Diethylene Glycol, freeze depressant, Dow | | 5.00 | |
| Morwet EFW Wetter, Witco | | 1.00 | |
| Imazethapyr Acid | 98.0 | 40.80 | 39.98 |
| Morwet D425, dispersant, Witco | | 3.00 | |

TABLE 1-continued

Example 1 Ingredients

| Ingredient | % AI-Tech | % Weight | % AI |
|---|---|---|---|
| 2% Kelzan - 0.5% Proxel Premix, thickener, Antimicrobial | | 5.00 | |
| Total | | 100 | |

Morwet EFW is a mixture of alkyl napthonate sulfonates.

Example 2

Example 2 is an exemplary suspension concentrate that includes a 4 lb. per gallon imidazolinone acid (imazethapyr acid), acidifying agent, anionic surfactant, anionic dispersant, and thickener.

TABLE 2

Example 2 Ingredients

| Ingredient | % AI-Tech | % Weight | % AI |
|---|---|---|---|
| Water | | 44.70 | |
| SAG 30 Antifoam, Witco | | 0.3 | |
| Diethylene Glycol, freeze depressant, Dow | | 4.00 | |
| Unite, Loveland Industries, surfactant & acidifier, anionic | | 1.00 | |
| Imazethapyr Acid | 98.0 | 42.00 | 41.16 |
| Soprophor FLK, Rhodia, Anionic dispersant | | 2.50 | |
| 72% Phosphoric Acid, acidifier | | 0.50 | |
| Attaflow FL, Englehard, clay thickener | | 5.00 | |
| Total | — | 100 | — |

Example 3

Example 3 is an exemplary suspension concentrate that includes a 4 lb. per gallon imidazolinone acid (imazethapyr acid), nonionic surfactant, nonionic dispersant, thickener, and anti-microbial agent.

TABLE 3

Example 3 Ingredients

| Ingredient | % AI-Tech | % Weight | % AI |
|---|---|---|---|
| Water | | 54.20 | |
| SAG 30 Antifoam, Witco | | 0.3 | |
| Propylene Glycol, freeze depressant, Dow | | 5.00 | |
| Surfonic L12-6, wetting agent, nonionic, Huntsman | | 1.00 | |
| Imazethapyr Acid | 98.0 | 31.00 | 30.38 |
| Tersperse 4894, dispersant, nonionic, Huntsman | | 3.00 | |

TABLE 3-continued

Example 3 Ingredients

| Ingredient | % AI-Tech | % Weight | % AI |
|---|---|---|---|
| 2% Kelzan - 0.5% Proxel Premix, thickener, Antimicrobial | | 5.00 | |
| Total | — | 100 | — |

Examples 4–5

The following examples illustrate how suspension concentrates of the invention can be used to control plant growth, optionally with an acidifying agent. PCC-1190 and PCC-1189 are examples of suspension concentrates having 3 pounds of active herbicide compound per gallon.

Materials and Methods

Examples 4–5 represent experiments conducted to evaluate the efficacy of a variety of different types of herbicide formulations, including formulations from suspension concentrates, and to evaluate the effect of adding acids to the spray solution as an acidifying agent (see Tables 4–6 for data from Example 4 and Tables 7 and 8 for data from Example 5). Each treatment in the experiment was replicated three times. An untreated control was also included in the experiment.

Examples 4–5 were designed to determine the effect of adding four different acidifying agents (i.e., PCC-1174, LI-136, sulfuric acid, and phosphoric acid) to formulations of imidazolinone acid (PCC-1190 and PCC-1189) and the effect of applying each formulation at six different rates (see data tables). These treatments were compared to PCC-1190 and PCC-1189 without the addition of an acidifying agent, a standard imidazolinone acid formulation (PURSUIT and SCEPTER), and an untreated control.

PCC-1189 Suspension Concentrate Formulation

PCC-1189 contains the active ingredient imazaquin acid.

| INGREDIENT | % AI-Tech | %/WT |
|---|---|---|
| Water | | 54.20 |
| SAG 30, OSI, Antifoam | | 0.30 |
| Proplyene Glycol, Antifreeze | | 5.00 |
| Surfonic L12-6, Huntsman, nonionic wetting agent | | 1.00 |
| Imazaquin Acid, Nat China, Active Ingredient | 95.00 | 31.00 |
| Tersperse 4894, Huntsman, nonionic dispersant/wetter | | 3.50 |
| Attaflow FL | | 5.00 |
| | | 100.00 |

Add in order listed to cowles high speed mixer stopping prior to Attaflow FL thickener addition.

Grind to 5–18 microns, 4 hrs in attritor, 60%.

Let down to mix tank with scales

Add calculated amount of thickener (accounting for amount of batch that stays in the attritor) to milled liquid. Blend moderately for 30 min.

PCC-1190 Suspension Concentrate Formulation

PCC-1190 contains the active ingredient imazethapyr acid.

| INGREDIENT | % AI-Tech | %/WT |
|---|---|---|
| Water | | 54.20 |
| SAG 30, OSI, Antifoam | | 0.30 |
| Proplyene Glycol, Antifreeze | | 5.00 |
| Surfonic L12-6, Huntsman, nonionic wetting agent | | 1.00 |
| Imazethapyr Acid, Nat China, Active Ingredient | 98.00 | 31.00 |
| Tersperse 4894, Huntsman, nonionic dispersat/wetter | | 3.50 |
| Attaflow FL | | 5.00 |
| | | 100.00 |

Add in order listed to cowles high speed mixer stopping prior to Attaflow FL thickener addition.
Grind to 5–18 microns, 4 hrs in attritor, 60%.
Let down to mix tank with scales
Add calculated amount of thickener (accounting for amount of batch that stays in the attritor) to milled liquid. Blend moderately for 30 min.
PURSUIT® is a commercially available product containing the active ingredient imazethapyr acid. PURSUIT® is formulated as a 2SL ("2SL" means a "two pound per gallon soluble liquid"). SCEPTER® is a commercially available product containing the active ingredient imazaquin acid.
Acidifying Agents
Sulfuric Acid—0.9%
Phosphoric Acid—0.9%
PCC-1174 Acidifying Agent
Commercially available as "AMADS," which is urea and $H_2SO_4$ in water:

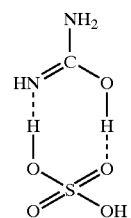

| INGREDIENT | %/WT |
|---|---|
| Water | 22.99 |
| 93% Sulfuric Acid | 48.65 |
| 99% Urea | 26.64 |
| Stepfac 8170 | 1.71 |
| SAG 10 Antifoam | 0.01 |

| | |
|---|---|
| Chemical Name | 1-amino methanamide dihydrogen tetraoxosulfate, or sulfuric acid and urea |
| Molecular Formula | $NH_2C(OH)NHSO_4H_2$ |

LI-136 acidifying agent
LI-136 is a blend of 50 wt. % 21-0-0 urea liquor and 50 wt percent of 72% phosphoric acid in water. The phrase "21-0-0 urea liquor" means a liquid that contains 21% by volume urea (nitrogen), 0% by volume phosphate (phosphorus), and 0% by volume potash (potassium).
Procedure
For the experiments, greenhouse flats 26 cm by 6 cm deep were filled with Metro Mix 350 potting soil. The soil was pre-wetted before filling the flats. Six furrows were pressed into the soil in each flat using a custom designed form. Corn, tame oats, velvet leaf (not used in Example 5), wheat, pinto beans, and sunflower were planted in each tray. One species was planted in each of the six rows in each flat. Five seeds were planted in each row of corn, pinto bean, and sunflower. Six seeds were planted in each row of tame oat and wheat. Because velvet leaf seeds were so small, the seeds were sprinkled in each row and the number of such seeds were not counted. Each flat was covered with 2 cm of Metro Mix 350 potting soil and placed in the greenhouse. Greenhouse conditions were 28/20 C day/night temperatures and 16/8 h day/night periods. Light was supplemented with 400 W sodium halide lights.

The plants were allowed to germinate and grow in the greenhouse for 2 weeks and then treated. Treatments were mixed using serial dilutions. Each dilution reduced the herbicide rate by one half. All acidifying agents (e.g., PCC-1174, LI-136, sulfuric acid, and phosphoric acid) were calculated and mixed to provide acid concentrations of 0.9%.

After mixing, the pH of the spray solution of each treatment was measured with a VWR Scientific model 8005 pH meter. The pH was measured to determine if the acid used or the amount of acid added was sufficient to lower the pH below the pKa of the acid herbicides used.

At the time of treatment, crops were at the following stages: corn—2 to 3 lf, tame oat—2 to 3 lf, velvet leaf—2 lf (not used in Example 5), pinto bean—2-3 lf, wheat—4 to 5 lf, and sunflower—2 lf. Plants were treated using a greenhouse track sprayer equipped with an 8001E nozzle and calibrated to deliver 140 L ha-1 at the height of the crop canopy. Each treatment was simultaneously applied to three trays of plants, one for each replicate. After treatment, the plants were left in the head house to dry and then transferred to the greenhouse. Plants in each treatment were evaluated visually for injury 1 week and 2 weeks after treatment.

TABLE 4

Summary of Variables of Example 4

| Acid Treatments | Volumes of each Acid (v/v %) | Herbicide | Herbicide Rate (lb AE/A) | Plants | Reps |
|---|---|---|---|---|---|
| PCC-1174 | 2 | PCC-1190 | 1 | Corn, | 3 |
| Sulfuric | | | 0.5 | Tame oat, | |
| Phosphoric | | | 0.25 | Velvet leaf, | |
| LI-136 | | | 0.125 | wheat | |
| | | | 0.063 | Pinto bean, | |
| | | | 0.0313 | Sunflower | |

Following are data that illustrate the efficacy of various herbicide compositions of Examples 4–5 and Summary of Variables of Example 5. The injury caused by the herbicide treatment was rated visually. Plants were observed and compared to the untreated control. All the plants of each species in each replication were given a single rating. A rating of 0=no injury—the plants look the same as the untreated. A rating of 100=dead—usually highly necrotic, brown and no chance of producing seed.

Each of the acids was combined with the PCC-1190 or PCC-1189 herbicide compositions to form a solution that contains 2 percent by volume of a given 0.9% (of the acid) concentrated acidifying agent (e.g., PCC-1174, LI-136, sulfuric acid, and phosphoric acid), as indicated in Tables 4–8, and such that the pH of the herbicide composition was below the pKa of the particular herbicide compound.

The ingredients of the herbicide compositions as applied are listed in the following tables, and were diluted with water and used at the rates indicated for herbicide ingredients and acidifying agents.

TABLE 5

Data for Example 4 (One Week)

| | Herbicide | Rate | Units | Corn | Tame Oat | Velvet Leaf | Wheat | Pinto Bean | Sunflower |
|---|---|---|---|---|---|---|---|---|---|
| 1 | PURSUIT | .0313 | LB AE/A | 0.0 | 10.0 | 50.0 | 10.0 | 10.0 | 50.0 |
| 2 | PURSUIT | 0.063 | LB AE/A | 0.0 | 20.0 | 50.0 | 20.0 | 10.0 | 50.0 |
| 3 | PURSUIT | 0.125 | LB AE/A | 0.0 | 30.0 | 50.0 | 20.0 | 20.0 | 50.0 |
| 4 | PURSUIT | 0.25 | LB AE/A | 0.0 | 50.0 | 50.0 | 20.0 | 30.0 | 70.0 |
| 5 | PURSUIT | 0.5 | LB AE/A | 0.0 | 60.0 | 50.0 | 30.0 | 40.0 | 90.0 |
| 6 | PURSUIT | 1 | LB AE/A | 10.0 | 60.0 | 50.0 | 50.0 | 40.0 | 98.0 |
| 7 | PCC-1190 | .0313 | LB AE/A | 0.0 | 10.0 | 50.0 | 10.0 | 10.0 | 50.0 |
| 8 | PCC-1190 | 0.063 | LB AE/A | 0.0 | 20.0 | 50.0 | 20.0 | 20.0 | 50.0 |
| 9 | PCC-1190 | 0.125 | LB AE/A | 0.0 | 30.0 | 50.0 | 20.0 | 20.0 | 60.0 |
| 10 | PCC-1190 | 0.25 | LB AE/A | 0.0 | 50.0 | 50.0 | 30.0 | 40.0 | 70.0 |
| 11 | PCC-1190 | 0.5 | LB AE/A | 0.0 | 60.0 | 50.0 | 40.0 | 40.0 | 90.0 |
| 12 | PCC-1190 | 1 | LB AE/A | 0.0 | 60.0 | 50.0 | 50.0 | 60.0 | 98.0 |
| 13 | PCC-1190 PCC-1174 | .0313 2 | LB AE/A % V/V | 0.0 | 20.0 | 50.0 | 10.0 | 10.0 | 50.0 |
| 14 | PCC-1190 PCC-1174 | 0.063 2 | LB AE/A % V/V | 0.0 | 20.0 | 50.0 | 10.0 | 10.0 | 50.0 |
| 15 | PCC-1190 PCC-1174 | .0125 2 | LB AE/A % V/V | 0.0 | 30.0 | 50.0 | 20.0 | 20.0 | 70.0 |
| 16 | PCC-1190 PCC-1174 | 0.25 2 | LB AE/A % V/V | 0.0 | 50.0 | 50.0 | 20.0 | 30.0 | 80.0 |
| 17 | PCC-1190 PCC-1174 | 0.5 2 | LB AE/A % V/V | 0.0 | 60.0 | 50.0 | 30.0 | 40.0 | 98.0 |
| 18 | PCC-1190 PCC-1174 | 1 2 | LB AE/A % V/V | 0.0 | 60.0 | 50.0 | 50.0 | 50.0 | 98.0 |
| 19 | PCC-1190 SULFURIC ACID | .0313 2 | LB AE/A % V/V | 0.0 | 10.0 | 50.0 | 10.0 | 10.0 | 40.0 |
| 20 | PCC-1190 SULFURIC ACID | 0.063 2 | LB AE/A % V/V | 0.0 | 20.0 | 50.0 | 20.0 | 20.0 | 50.0 |
| 21 | PCC-1190 SULFURIC ACID | .0125 2 | LB AE/A % V/V | 0.0 | 30.0 | 50.0 | 20.0 | 30.0 | 50.0 |
| 22 | PCC-1190 SULFURIC ACID | 0.25 2 | LB AE/A % V/V | 0.0 | 40.0 | 50.0 | 30.0 | 50.0 | 80.0 |
| 23 | PCC-1190 SULFURIC ACID | 0.5 2 | LB AE/A % V/V | 0.0 | 50.0 | 60.0 | 50.0 | 50.0 | 90.0 |
| 24 | PCC-1190 SULFURIC ACID | 1 2 | LB AE/A % V/V | 0.0 | 60.0 | 60.0 | 50.0 | 60.0 | 98.0 |
| 25 | PCC-1190 PHOSPHORIC ACID | .0313 2 | LB AE/A % V/V | 0.0 | 10.0 | 50.0 | 10.0 | 10.0 | 50.0 |
| 26 | PCC-1190 PHOSPHORIC ACID | 0.063 2 | LB AE/A % V/V | 0.0 | 20.0 | 50.0 | 10.0 | 10.0 | 50.0 |
| 27 | PCC-1190 PHOSPHORIC ACID | .0125 2 | LB AE/A % V/V | 0.0 | 20.0 | 50.0 | 10.0 | 20.0 | 50.0 |
| 28 | PCC-1190 PHOSPHORIC ACID | 0.25 2 | LB AE/A % V/V | 0.0 | 30.0 | 50.0 | 30.0 | 30.0 | 50.0 |
| 29 | PCC-1190 PHOSPHORIC ACID | 0.5 2 | LB AE/A % V/V | 0.0 | 40.0 | 50.0 | 40.0 | 40.0 | 70.0 |
| 30 | PCC-1190 PHOSPHORIC ACID | 1 2 | LB AE/A % V/V | 0.0 | 40.0 | 50.0 | 50.0 | 50.0 | 90.0 |
| 31 | PCC-1190 LI 136 | .0313 2 | LB AE/A % V/V | 0.0 | 10.0 | 50.0 | 10.0 | 10.0 | 50.0 |
| 32 | PCC-1190 LI 136 | 0.063 2 | LB AE/A % V/V | 0.0 | 10.0 | 50.0 | 10.0 | 10.0 | 50.0 |
| 33 | PCC-1190 LI 136 | .0125 2 | LB AE/A % V/V | 0.0 | 20.0 | 50.0 | 20.0 | 20.0 | 50.0 |
| 34 | PCC-1190 LI 136 | 0.25 2 | LB AE/A % V/V | 0.0 | 40.0 | 50.0 | 20.0 | 30.0 | 70.0 |
| 35 | PCC-1190 LI 136 | 0.5 2 | LB AE/A % V/V | 0.0 | 40.0 | 50.0 | 30.0 | 30.0 | 70.0 |
| 36 | PCC-1190 LI 136 | 1 2 | LB AE/A % V/V | 0.0 | 50.0 | 50.0 | 40.0 | 40.0 | 95.0 |
| 37 | UNTREATED | | | 0.0 | 0.0 | 0.0 | 0.0 | 0.0 | 0.0 |

TABLE 6

Data for Example 4 (Two Week)

| | Herbicide | Rate | Units | Corn | Tame Oat | Velvet Leaf | Wheat | Pinto Bean | Sunflower |
|---|---|---|---|---|---|---|---|---|---|
| 1 | PURSUIT | .0313 | LB AE/A | 20.0 | 20.0 | 50.0 | 20.0 | 30.0 | 50.0 |
| 2 | PURSUIT | 0.063 | LB AE/A | 20.0 | 20.0 | 50.0 | 20.0 | 30.0 | 50.0 |
| 3 | PURSUIT | 0.125 | LB AE/A | 20.0 | 40.0 | 50.0 | 30.0 | 35.0 | 50.0 |
| 4 | PURSUIT | 0.25 | LB AE/A | 20.0 | 50.0 | 60.0 | 40.0 | 35.0 | 70.0 |
| 5 | PURSUIT | 0.5 | LB AE/A | 20.0 | 70.0 | 60.0 | 70.0 | 45.0 | 95.0 |
| 6 | PURSUIT | 1 | LB AE/A | 20.0 | 80.0 | 70.0 | 75.0 | 55.0 | 100.0 |
| 7 | PCC-1190 | .0313 | LB AE/A | 10.0 | 20.0 | 50.0 | 20.0 | 25.0 | 50.0 |
| 8 | PCC-1190 | 0.063 | LB AE/A | 20.0 | 30.0 | 50.0 | 30.0 | 35.0 | 70.0 |
| 9 | PCC-1190 | 0.125 | LB AE/A | 30.0 | 60.0 | 50.0 | 30.0 | 35.0 | 70.0 |
| 10 | PCC-1190 | 0.25 | LB AE/A | 20.0 | 70.0 | 60.0 | 50.0 | 40.0 | 90.0 |
| 11 | PCC-1190 | 0.5 | LB AE/A | 20.0 | 70.0 | 60.0 | 70.0 | 50.0 | 95.0 |
| 12 | PCC-1190 | 1 | LB AE/A | 20.0 | 85.0 | 70.0 | 75.0 | 65.0 | 100.0 |
| 13 | PCC-1190 PCC-1174 | .0313 2 | LB AE/A % V/V | 10.0 | 50.0 | 50.0 | 25.0 | 30.0 | 70.0 |
| 14 | PCC-1190 PCC-1174 | 0.063 2 | LB AE/A % V/V | 10.0 | 50.0 | 50.0 | 40.0 | 30.0 | 80.0 |
| 15 | PCC-1190 PCC-1174 | .0125 2 | LB AE/A % V/V | 10.0 | 60.0 | 50.0 | 40.0 | 30.0 | 85.0 |
| 16 | PCC-1190 PCC-1174 | 0.25 2 | LB AE/A %V/V | 10.0 | 70.0 | 60.0 | 50.0 | 50.0 | 95.0 |
| 17 | PCC-1190 PCC-1174 | 0.5 2 | LB AE/A % V/V | 20.0 | 80.0 | 60.0 | 75.0 | 50.0 | 95.0 |
| 18 | PCC-1190 PCC-1174 | 1 2 | LB AE/A % V/V | 20.0 | 90.0 | 70.0 | 85.0 | 70.0 | 100.0 |
| 19 | PCC-1190 SULFURIC ACID | .0313 2 | LB AE/A % V/V | 20.0 | 50.0 | 50.0 | 25.0 | 30.0 | 70.0 |
| 20 | PCC-1190 SULFURIC ACID | 0.063 2 | LB AE/A % V/V | 30.0 | 50.0 | 50.0 | 40.0 | 40.0 | 80.0 |
| 21 | PCC-1190 SULFURIC ACID | .0125 2 | LB AE/A % V/V | 23.3 | 60.0 | 50.0 | 40.0 | 35.0 | 85.0 |
| 22 | PCC-1190 SULFURIC ACID | 0.25 2 | LB AE/A % V/V | 20.0 | 70.0 | 60.0 | 50.0 | 50.0 | 95.0 |
| 23 | PCC-1190 SULFURIC ACID | 0.5 2 | LB AE/A % V/V | 10.0 | 80.0 | 65.0 | 75.0 | 65.0 | 95.0 |
| 24 | PCC-1190 SULFURIC ACID | 1 2 | LB AE/A % V/V | 20.0 | 95.0 | 70.0 | 85.0 | 80.0 | 100.0 |
| 25 | PCC-1190 PHOSPHORIC ACID | .0313 2 | LB AE/A % V/V | 10.0 | 50.0 | 50.0 | 25.0 | 30.0 | 70.0 |
| 26 | PCC-1190 PHOSPHORIC ACID | 0.063 2 | LB AE/A % V/V | 20.0 | 50.0 | 50.0 | 40.0 | 30.0 | 80.0 |
| 27 | PCC-1190 PHOSPHORIC ACID | .0125 2 | LB AE/A % V/V | 10.0 | 56.7 | 50.0 | 35.0 | 30.0 | 85.0 |
| 28 | PCC-1190 PHOSPHORIC ACID | 0.25 2 | LB AE/A % V/V | 20.0 | 66.7 | 60.0 | 50.0 | 40.0 | 95.0 |
| 29 | PCC-1190 PHOSPHORIC ACID | 0.5 2 | LB AE/A % V/V | 20.0 | 70.0 | 60.0 | 75.0 | 50.0 | 95.0 |
| 30 | PCC-1190 PHOSPHORIC ACID | 1 2 | LB AE/A % V/V | 20.0 | 76.7 | 70.0 | 75.0 | 70.0 | 100.0 |
| 31 | PCC-1190 LI 136 | .0313 2 | LB AE/A % V/V | 10.0 | 46.7 | 50.0 | 20.0 | 25.0 | 60.0 |
| 32 | PCC-1190 LI 136 | 0.063 2 | LB AE/A % V/V | 0.0 | 30.0 | 50.0 | 30.0 | 25.0 | 80.0 |
| 33 | PCC-1190 LI 136 | .0125 2 | LB AE/A % V/V | 10.0 | 30.0 | 50.0 | 30.0 | 30.0 | 70.0 |
| 34 | PCC-1190 LI 136 | 0.25 2 | LB AE/A % V/V | 15.0 | 50.0 | 60.0 | 35.0 | 30.0 | 85.0 |
| 35 | PCC-1190 LI 136 | 0.5 2 | LB AE/A % V/V | 20.0 | 63.3 | 60.0 | 50.0 | 45.0 | 90.0 |
| 36 | PCC-1190 LI 136 | 1 2 | LB AE/A % V/V | 20.0 | 80.0 | 70.0 | 60.0 | 55.0 | 96.7 |
| 37 | UNTREATED | | | 0.0 | 0.0 | 0.0 | 0.0 | 0.0 | 0.0 |

TABLE 7

Summary of Variables of Example 5

| Acid Treatments | Volumes of each Acid (v/v %) | Herbicide | Herbicide Rate (lb AE/A) | Plants | Reps |
|---|---|---|---|---|---|
| PCC-1174 | 2 | PCC-1189 | 0.0155 | Corn, | 3 |
| Sulfuric | | | 0.031 | Tame oat, | |
| Phosphoric | | | 0.0613 | Wheat, | |
| LI-136 | | | 0.1225 | | |
| | | | 0.245 | Pinto bean, | |
| | | | 0.49 | Sunflower | |

TABLE 8

Data for Example 5 (Two Week)

| | Herbicide | Rate | Unit | Corn | Tame Oat | Wheat | Pinto Bean | Sunflower |
|---|---|---|---|---|---|---|---|---|
| 1 | SCEPTER | .0155 | LB AE/A | 0.0 | 0.0 | 0.0 | 0.0 | 0.0 |
| 2 | SCEPTER | 0.031 | LB AE/A | 0.0 | 0.0 | 10.0 | 20.0 | 30.0 |
| 3 | SCEPTER | .0613 | LB AE/A | 0.0 | 0.0 | 0.0 | 10.0 | 10.0 |
| 4 | SCEPTER | .1225 | LB AE/A | 10.0 | 0.0 | 0.0 | 0.0 | 30.0 |
| 5 | SCEPTER | 0.245 | LB AE/A | 10.0 | 0.0 | 0.0 | 20.0 | 60.0 |
| 6 | SCEPTER | 0.49 | LB AE/A | 20.0 | 10.0 | 10.0 | 20.0 | 60.0 |
| 7 | PCC-1189 | .0155 | LB AE/A | 30.0 | 10.0 | 10.0 | 0.0 | 0.0 |
| 8 | PCC-1189 | 0.031 | LB AE/A | 0.0 | 0.0 | 0.0 | 10.0 | 10.0 |
| 9 | PCC-1189 | .0613 | LB AE/A | 20.0 | 10.0 | 0.0 | 10.0 | 10.0 |
| 10 | PCC-1189 | .1225 | LB AE/A | 20.0 | 10.0 | 10.0 | 10.0 | 60.0 |
| 11 | PCC-1189 | 0.245 | LB AE/A | 40.0 | 20.0 | 10.0 | 20.0 | 60.0 |
| 12 | PCC-1189 | 0.49 | LB AE/A | 30.0 | 10.0 | 10.0 | 10.0 | 70.0 |
| 13 | PCC-1189 | .0155 | LB AE/A | 30.0 | 20.0 | 10.0 | 10.0 | 20.0 |
| 13 | PCC-1174 | 2 | % V/V | | | | | |
| 14 | PCC-1189 | 0.031 | LB AE/A | 10.0 | 20.0 | 10.0 | 20.0 | 70.0 |
| 14 | PCC-1174 | 2 | % V/V | | | | | |
| 15 | PCC-1189 | .0613 | LB AE/A | 30.0 | 30.0 | 20.0 | 30.0 | 60.0 |
| 15 | PCC-1174 | 2 | % V/V | | | | | |
| 16 | PCC-1189 | .1225 | LB AE/A | 40.0 | 30.0 | 20.0 | 30.0 | 70.0 |
| 16 | PCC-1174 | 2 | % V/V | | | | | |
| 17 | PCC-1189 | 0.245 | LB AE/A | 50.0 | 30.0 | 20.0 | 40.0 | 60.0 |
| 17 | PCC-1174 | 2 | % V/V | | | | | |
| 18 | PCC-1189 | 0.49 | LB AE/A | 50.0 | 10.0 | 10.0 | 60.0 | 90.0 |
| 18 | PCC-1174 | 2 | % V/V | | | | | |
| 19 | PCC-1189 | .0155 | LB AE/A | 10.0 | 0.0 | 0.0 | 10.0 | 30.0 |
| 19 | SULFURIC ACID | 2 | % V/V | | | | | |
| 20 | PCC-1189 | 0.031 | LB AE/A | 20.0 | 0.0 | 0.0 | 10.0 | 30.0 |
| 20 | SULFURIC ACID | 2 | % V/V | | | | | |
| 21 | PCC-1189 | .0613 | LB AE/A | 10.0 | 0.0 | 0.0 | 0.0 | 40.0 |
| 21 | SULFURIC ACID | 2 | % V/V | | | | | |
| 22 | PCC-1189 | .1225 | LB AE/A | 10.0 | 0.0 | 0.0 | 10.0 | 40.0 |
| 22 | SULFURIC ACID | 2 | % V/V | | | | | |
| 23 | PCC-1189 | 0.245 | LB AE/A | 20.0 | 0.0 | 0.0 | 20.0 | 60.0 |
| 23 | SULFURIC ACID | 2 | % V/V | | | | | |
| 24 | PCC-1189 | 0.49 | LB AE/A | 20.0 | 10.0 | 10.0 | 30.0 | 80.0 |
| 24 | SULFURIC ACID | 2 | % V/V | | | | | |
| 25 | PCC-1189 | .0155 | LB AE/A | 10.0 | 0.0 | 0.0 | 10.0 | 50.0 |
| 25 | PHOSPHORIC ACID | 2 | % V/V | | | | | |
| 26 | PCC-1189 | 0.031 | LB AE/A | 10.0 | 0.0 | 0.0 | 20.0 | 50.0 |
| 26 | PHOSPHORIC ACID | 2 | % V/V | | | | | |
| 27 | PCC-1189 | .0613 | LB AE/A | 15.0 | 0.0 | 0.0 | 30.0 | 40.0 |
| 27 | PHOSPHORIC ACID | 2 | % V/V | | | | | |
| 28 | PCC-1189 | .1225 | LB AE/A | 10.0 | 0.0 | 0.0 | 25.0 | 50.0 |
| 28 | PHOSPHORIC ACID | 2 | % V/V | | | | | |
| 29 | PCC-1189 | 0.245 | LB AE/A | 10.0 | 0.0 | 0.0 | 30.0 | 60.0 |
| 29 | PHOSPHORIC ACID | 2 | % V/V | | | | | |
| 30 | PCC-1189 | 0.49 | LB AE/A | 20.0 | 0.0 | 0.0 | 30.0 | 50.0 |
| 30 | PHOSPHORIC ACID | 2 | % V/V | | | | | |
| 31 | PCC-1189 | .0155 | LB AE/A | 20.0 | 0.0 | 0.0 | 10.0 | 20.0 |
| 31 | LI136 | 2 | % V/V | | | | | |
| 32 | PCC-1189 | 0.031 | LB AE/A | 20.0 | 0.0 | 0.0 | 10.0 | 10.0 |
| 32 | LI136 | 2 | % V/V | | | | | |

TABLE 8-continued

Data for Example 5 (Two Week)

| Herbicide | Rate | Unit | Corn | Tame Oat | Wheat | Pinto Bean | Sunflower |
|---|---|---|---|---|---|---|---|
| 33 PCC-1189 | .0613 | LB AE/A | 10.0 | 0.0 | 0.0 | 10.0 | 30.0 |
| 33 LI136 | 2 | % V/V | | | | | |
| 34 PCC-1189 | .1225 | LB AE/A | 30.0 | 20.0 | 20.0 | 30.0 | 20.0 |
| 34 LI136 | 2 | % V/V | | | | | |
| 35 PCC-1189 | 0.245 | LB AE/A | 30.0 | 10.0 | 10.0 | 30.0 | 40.0 |
| 35 LI136 | 2 | % V/V | | | | | |
| 36 PCC-1189 | 0.49 | LB AE/A | 10.0 | 0.0 | 0.0 | 20.0 | 70.0 |
| 36 LI136 | 2 | % V/V | | | | | |
| 37 Untreated | | | 0.0 | 0.0 | 0.0 | 0.0 | 0.0 |

We claim:

1. A herbicide composition comprising
   a suspension concentrate comprising an imidazolinone acid, and
   acidifying agent other than sulfuric acid in an amount so the pH of the composition is below the pKa of the imidazolinone acid.

2. The composition of claim 1 wherein the pH of the composition is below about 4.0.

3. The composition of claim 1 comprising an acidifying agent selected from the group consisting of: hydrochloric acid, nitric acid, acetic acid, phosphoric acid, perchloric acid, polyphosphoric acid, and combinations thereof.

4. The composition of claim 3 wherein the composition does not include sulfuric acid.

5. The composition of claim 3 wherein the composition does not include an adduct of sulfuric acid and an amide of the formula:

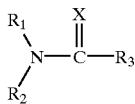

wherein X is chalcogen, and each of $R_1$, $R_2$, and $R_3$ is independently selected from hydrogen and organic radicals.

6. The composition of claim 1 wherein the acidifying agent comprises an adduct of sulfuric acid and an amide of the formula:

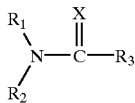

wherein X is chalcogen, and each of $R_1$, $R_2$, and $R_3$ is independently selected from hydrogen and organic radicals.

7. The composition of claim 6 wherein the adduct is an adduct of sulfuric acid and urea.

8. The composition of claim 1 wherein the imidazolinone acid is chosen from the group consisting of imazethapyr acid, imazaquin acid, imazapyr acid, imazamethabenz acid, imazapic acid, imazamox acid, and combinations thereof.

9. The composition of claim 1 wherein the suspension concentrate comprises surfactant selected from nonionic surfactant, anionic surfactant, cationic surfactant, and mixtures thereof.

10. The composition of claim 1 comprising alcohol alkoxylate nonionic surfactant having the formula $$R-O-((CH_2)_xO)_y-H$$

wherein R is a branched or linear alkyl, x is in the range from 2 to 5, and y is in the range from 5 to 25.

11. The composition of claim 10 wherein R is a short chain branched or linear alcohol having from about 3 to 23 carbon atoms.

12. The composition of claim 1 comprising linear alcohol ethoxylate nonionic surfactant of the formula:

$$CH_3(C_2H_4)_mO(C_2H_4O)_nH$$

wherein m is in the range from 1 to 11 and n is in the range from about 5 to 25.

13. The composition of claim 1 comprising linear alcohol propoxylate nonionic surfactant of the formula:

$$CH_3(C_2H_4)_mO(C_3H_6O)_nH,$$

wherein m is in the range from 1 to 11 carbon atoms and n is in the range from about 5 to 25.

14. The composition of claim 1 comprising anionic surfactant selected from the group consisting of sodium alkyl naphthalene sulfonate, sodium butyl naphthalene sulfonate, sodium di-n-butyl naphthalene sulfonate, sodium diisopropyl naphthalene sulfonate, sodium dimethyl naphthalene sulfonate, ethoxylated tristyrylphenol phosphate potassium salt, and mixtures thereof.

15. A herbicide composition comprising:
    aqueous suspension concentrate comprising
       about 25 to about 45 weight percent imidazolinone acid, and
       about 0.5 to about 1.5 weight percent surfactant selected from the group consisting of: short chain alcohol ethoxylate nonionic surfactant, anionic surfactant, cationic surfactant, and mixtures thereof, and
       about 40 to about 60 parts by weight water; and
    acidifying agent selected from the group consisting of sulfuric acid, hydrochloric acid, nitric acid, acetic acid, phosphoric acid, perchloric acid, polyphosphoric acid, an adduct of sulfuric acid and urea, and combinations thereof, in an amount so the pH of the composition is below the pKa of the imidazolinone acid.

16. An aqueous suspension concentrate comprising imidazolinone acid and a short chain alcohol ethoxylate nonionic surfactant having a short chain branched or linear alkyl having from 3 to 23 carbon atoms.

17. The suspension concentrate of claim 16 wherein the nonionic surfactant comprises short chain linear alcohol ethoxylate surfactant.

18. The suspension concentrate of claim 16 wherein the nonionic surfactant has the formula:

$$CH_3(C_2H_4)_mO(C_2H_4O)_nH$$

wherein m is in the range from 1 to 11 and n is in the range from about 5 to 25.

19. The suspension concentrate of claim 16 comprising from greater than 30 to about 50 parts by weight imidazolinone acid per 1 part by weight surfactant.

20. A herbicide composition comprising suspension concentrate of claim 16 and acidifying agent.

21. The suspension concentrate of claim 16 containing essentially no organic solvent.

22. The suspension concentrate of claim 16 wherein the imidazolinone acid is selected from the group consisting of imazethapyr acid, imazaquin acid, imazapyr acid, imazamethabenz acid, imazapic acid, imazamox acid, and combinations thereof.

23. An aqueous suspension concentrate comprising an imidazolinone acid and anionic surfactant.

24. A herbicide composition comprising suspension concentrate of claim 23 and acidifying agent.

25. The suspension concentrate of claim 23 wherein the anionic surfactant comprises a sodium alkyl naphthalene sulfonate surfactant.

26. The suspension concentrate of claim 25 wherein the anionic surfactant is selected from the group consisting of sodium butyl naphthalene sulfonate, sodium di-n-butyl naphthalene sulfonate, sodium diisopropyl naphthalene sulfonate, sodium dimethyl naphthalene sulfonate, and mixtures thereof.

27. The suspension concentrate of claim 23 wherein the anionic surfactant comprises an ethoxylated tristyrylphenol phosphate salt.

28. The suspension concentrate of claim 27 wherein the anionic surfactant comprises ethoxylated tristyrylphenol phosphate potassium salt.

29. A suspension concentrate comprising imidazolinone acid and surfactant, comprising from greater than 30 parts by weight imidazolinone acid to about 50 parts by weight imidazolinone acid, per 1 part by weight surfactant.

30. The suspension concentrate of claim 29 wherein the suspension concentrate is an aqueous suspension concentrate.

31. The suspension concentrate of claim 29 comprising from 31 to 45 parts by weight imidazolinone acid per 1 part by weight surfactant.

32. The composition of claim 29 further comprising from about 2 to about 5 weight percent dispersant.

33. A herbicide composition comprising
   imidazolinone acid, and
   acidifying agent other than sulfuric acid in an amount so the pH of the composition is below the pKa of the imidazolinone acid.

34. The herbicide composition of claim 33 comprising additional active herbicide compound.

35. The herbicide composition of claim 34 wherein the additional active herbicide compound is an acid form of active herbicide compound.

36. The herbicide composition of claim 35 wherein the additional active herbicide compound is glyphosate acid.

37. A herbicide composition comprising:
   aqueous suspension concentrate comprising
      about 25 to about 45 weight percent imidazolinone acid, and
      about 0.5 to about 1.5 weight percent surfactant selected from the group consisting of: nonionic surfactant, anionic surfactant, cationic surfactant, and mixtures thereof, and
      about 40 to about 60 parts by weight water; and
   acidifying agent selected from the group consisting of hydrochloric acid, nitric acid, acetic acid, phosphoric acid, perchloric acid, and polyphosphoric acid, an adduct of sulfuric acid and urea, and combinations thereof, in an amount so the pH of the composition is below the pKa of the imidazolinone acid.

38. A method of killing or controlling unwanted vegetation growth, the method comprising preparing a herbicide composition comprising an imidazolinone acid and an amount of acidifying agent other than sulfuric acid to reduce the pH of the herbicide composition to a pH below the pKa of the imidazolinone acid, and applying the herbicide composition to control plant growth.

39. A method of killing or controlling unwanted vegetation growth, the method comprising preparing a herbicide composition comprising an aqueous suspension concentrate comprising an imidazolinone acid and surfactant selected from the group consisting of short chain alcohol ethoxylate nonionic surfactant, anionic surfactant, cationic surfactant, and mixtures thereof, and applying the herbicide composition to control plant growth.

40. The method of claim 39 wherein the herbicide composition comprises acidifying agent to reduce the pH of the herbicide composition to below the pKa of the imidazolinone acid, the acidifying agent selected from the group consisting of sulfuric acid, hydrochloric acid, nitric acid, acetic acid, phosphoric acid, perchloric acid, and polyphosphoric acid, and an adduct of sulfuric acid and an amide adduct of the formula:

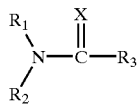

wherein X is chalcogen, and each of $R_1$, $R_2$, and $R_3$ is independently selected from hydrogen and organic radicals.

41. The method of claim 40 wherein the acidifying agent is selected from the group consisting of phosphoric acid, polyphosphoric acid, and an adduct of urea and sulfuric acid.

42. A method of preparing a herbicide composition comprising imidazolinone acid, the method comprising combining imidazolinone acid particles with water and surfactant, mixing or agitating the water, imidazolinone acid particles, and surfactant, wet milling water, imidazolinone acid particles, and surfactant to produce a suspension concentrate, and combining the suspension concentrate with acidifying agent in an amount to produce a herbicide composition having a pH below the pKa of the imidazolinone acid.

43. A method of preparing an aqueous suspension concentrate, the method comprising
   combining imidazolinone particles with surfactant and water, the surfactant comprising a surfactant selected from the group consisting of: a short chain alcohol ethoxylate nonionic surfactant, anionic surfactant, cationic surfactant, and mixtures thereof,
   mixing the water, imidazolinone particles, and surfactant, and
   wet milling the mixture to produce a suspension concentrate.

44. The herbicide composition of claim 43 comprising additional active herbicide compound.

45. The herbicide composition of claim 44 wherein the additional active herbicide compound is a herbicide compound in acid form.

46. The herbicide composition of claim 45 wherein the additional herbicide compound in acid form is glyphosate acid.

* * * * *